US008351741B2

(12) United States Patent
Tang et al.

(10) Patent No.: US 8,351,741 B2
(45) Date of Patent: *Jan. 8, 2013

(54) SENSITIVE EMISSION LIGHT GATHERING AND FLOW THROUGH DETECTION SYSTEM

(75) Inventors: Cha-Mei Tang, Potomac, MD (US); Platte T. Amstutz, III, Vienna, VA (US)

(73) Assignee: Creatv MicroTech, Inc., Potomac, MD (US)

( * ) Notice: Subject to any disclaimer, the term of this patent is extended or adjusted under 35 U.S.C. 154(b) by 606 days.

This patent is subject to a terminal disclaimer.

(21) Appl. No.: 12/494,152

(22) Filed: Jun. 29, 2009

(65) Prior Publication Data

US 2010/0002981 A1 Jan. 7, 2010

Related U.S. Application Data

(63) Continuation-in-part of application No. 11/705,606, filed on Feb. 13, 2007, now Pat. No. 7,565,042, which is a continuation-in-part of application No. 11/541,785, filed on Oct. 3, 2006, now Pat. No. 7,801,394.

(60) Provisional application No. 60/722,428, filed on Oct. 3, 2005.

(51) Int. Cl.
*G02B 6/32* (2006.01)
*G02B 6/42* (2006.01)
*G02B 6/00* (2006.01)

(52) U.S. Cl. ............... 385/12; 385/31; 385/33; 385/38; 385/39; 385/49

(58) Field of Classification Search .................... 385/12
See application file for complete search history.

(56) References Cited

U.S. PATENT DOCUMENTS

| | | | |
|---|---|---|---|
| 4,867,559 A | 9/1989 | Bach | |
| 5,933,565 A | 8/1999 | Diebold et al. | |
| 6,188,813 B1 | 2/2001 | Dourdeville et al. | |
| 6,332,049 B1 | 12/2001 | Dasgupta | |
| 6,652,809 B1 * | 11/2003 | Comley et al. | 422/82.05 |
| 6,813,427 B1 | 11/2004 | Kaltenbacher | |
| 7,155,082 B2 | 12/2006 | Oakey et al. | |
| 7,565,042 B2 * | 7/2009 | Tang et al. | 385/12 |
| 2002/0037130 A1 | 3/2002 | McBride | |
| 2003/0161572 A1 | 8/2003 | Johnck | |
| 2006/0068412 A1 * | 3/2006 | Tang | 435/6 |
| 2006/0171846 A1 | 8/2006 | Marr et al. | |

FOREIGN PATENT DOCUMENTS

CN 2166469 Y 5/1994

* cited by examiner

*Primary Examiner* — Ryan Lepisto
(74) *Attorney, Agent, or Firm* — Roylance, Abrams, Berdo and Goodman L.L.P.

(57) ABSTRACT

A method of detecting fluorescence/absorbance/luminescence from 24-well, 48-well, 96-well, 384-well and 1536-well microplates and other sample containers. The sample is pumped into a waveguide. The waveguide efficiently gathers and guides the emission light to the end of the waveguide. The emission light exits the ends of the waveguide and is focused into a detector. To minimize background caused by the excitation light used for fluorescence, the excitation illuminates the waveguides at 90 degrees. To facilitate reuse, the waveguide assembly can be configured to be washed by an appropriate wash solution.

30 Claims, 29 Drawing Sheets

(a) (b)

SENSITIVE EMISSION LIGHT GATHERING AND FLOW THROUGH DETECTION SYSTEM

This application is a continuation in part of U.S. patent application Ser. No. 11/705,606, filed Feb. 13, 2007, now U.S. Pat. No. 7,565,042 which is a continuation in part of U.S. patent application Ser. No. 11/541,785 filed Oct. 3, 2006, now U.S. Pat. No. 7,801,394 which claims benefit under 35 U.S.C. §119 from U.S. Provisional Application No. 60/722,428, filed on Oct. 3, 2005, the entire contents of all of which are incorporated herein by reference.

FIELD OF THE INVENTION

The invention relates to a sensitive luminescence flow through detection system including at the minimum a waveguide that can allow a liquid or gaseous sample to flow through the inside of the waveguide. The invention also relates to a fluorescent flow through detection system that can include an excitation light source and a sensitive detection system to detect the change of both the excitation and emission light signals from a sample contained or flowing inside a waveguide. The flow through waveguide is efficient in gathering and guiding the emission light to the detector. The waveguide design, the arrangement of the excitation light illumination, and optical filters may be configured to facilitate detection of very low concentrations of matter of interest in the sample and emission reagents and for ease of use. This detection method is applied to reading the light signal from the 24-well, 48-well, 96-well, 384-well and 1536-well plates or microplate commonly used for biological assays.

DESCRIPTION OF RELATED ART

As used herein, the term "Integrating Waveguide Sensor" technologies refer to the detection of excitation and/or emission signals from luminescence, absorbance, and/or fluorescence from matter on the surface of a waveguide or in solution contained inside or flowing through a waveguide.

The solid phase implementation of the Integrating Waveguide Sensor is based on detection using emission reagents attached to the surface of a waveguide, but not utilizing liquid next to the waveguide for guiding the emission signal. A light source appropriate to the emission reagent illuminates the surface of the waveguide at a 90-degree angle. The optical signal emitted by matter on the surface of the waveguide is efficiently gathered by the waveguide and exits from the end of the waveguide. The emitted signal is sent to the detector via a set of lenses and filters. This technique is described in Mark J. Feldstein, Brian D. MacCraith and Frances S. Ligler, "Integrating Multi-Waveguide Sensor," U.S. Pat. No. 6,137,117 issued on Oct. 24, 2000, and in Frances S. Ligler, Marc Breimer, Joel P. Golden, Delana A. Nivens, James P. Dodson, Tiffanee M. Green, Daniel P. Haders, and Omowunmi A. Sadik, "Integrating Waveguide Biosensor," Anal. Chem. 2002, 74, 713-719, and the entire disclosures of both of these documents is incorporated herein by reference.

A liquid phase of Integrating Waveguide Sensor was described in U.S. Patent and Trademark Application Ser. No. 60/722,428, "Sensitive Emission Light Gathering and Detection System," by Cha-Mei Tang and Platte T. Amstutz, III. In this application, the liquid sample is inside the waveguide. The size of the sample that can be analyzed is restricted to the volume that can be contained inside the waveguide.

A flow through Integrating Waveguide Sensor technology was described in U.S. Patent and Trademark application Ser. No. 11/073,430, "Flow-Through Chemical and Biological Sensor", by Cha-Mei Tang and Platte T. Amstutz, III. In this application, the fluid sample solution surrounds the waveguide(s), and the size of the sample that can be analyzed is not restricted.

SUMMARY OF THE INVENTION

An object of the present invention is the liquid phase implementation of the Integrating Waveguide Sensor where the absorption and/or emission reagents are in a fluid sample inside a container with an inlet and outlet that allows the sample to flow through the container, where the components of the container and the sample together act like a waveguide.

For fluorescence and absorbance applications, a light source appropriate to the absorption and/or emission reagent illuminates the waveguide containing the sample from a direction perpendicular to or at an angle to the surface(s) of the waveguide. The emitted signal is gathered by the waveguide, along with excitation light, and exits from the end of the waveguide. The excitation and emission signals are sent to the detector via a set of lenses and filters.

For luminescence applications, an excitation light source is not needed. The emitted signal is gathered by the waveguide, and exits from the end of the waveguide. The emission signal is sent to the detector via a set of lenses and filters.

As used herein, the term "sample" is intended to mean predominantly a liquid, and the liquid might also contain a variety of other materials, such as small solid particles, chemicals, molecules, proteins, DNA, emission reagents, microorganisms, cells, and any other desired matter.

As used herein, the term "gaseous sample" is to be distinguished from "sample"

As used herein, the term "optical elements" includes elements comprising any one, or a combination, of lens(es), filter(s), optical waveguide(s) (such as optical fibers, but excluding the flow through waveguide itself), and gratings. The optical elements are used (1) to increase the signal (the emission light) which is increased by improved collection of emission light and improved guiding of the light to the detector using, for example, lens(es) and optical waveguides (such as optical fibers) and (2) to reduce noise, background and/or other undesirable sources of light by eliminating light from undesirable wavelengths using filter(s), gratings, etc.

As used herein, the term "waveguide assembly" refers to the waveguide, the connection of the waveguide to the tubing including a transparent opening of the connector to allow the emission light generated within the waveguide assembly to propagate to the detector.

As used herein, the term "flow through waveguide" refers to the waveguide assembly that allows a sample to enter and exit, the combination of the sample and the waveguide assembly acting as a waveguide to guide emission light generated by light-absorbing and/or light-generating matter in the sample to the detector.

As used herein, the terms "emission light" and/or "emission signal," refer to the light produced by luminescence, fluorescence, phosphorescence and/or other emission reagents.

As used herein, the term "luminescence" refers to the production of electromagnetic radiation by a chemical or biochemical material that is used as or produced by an emission reagent. "Chemiluminescent" refers to the production of light when the excitation energy derived from a chemical reaction. "Bioluminescent" refers to a subset of chemiluminescence, where the light is produced by biological or biochemical reaction. A specific example of bioluminescence is the production of light by a firefly where the substrate luciferin combines with the enzyme luciferase and reactants ATP (adenosine triphosphate) and oxygen. "Electrochemiluminescence (ECL)" is a form of luminescence in which the light emitting chemiluminescent reaction is preceded by an electrochemical reaction.

As used herein, the term "fluorescence" refers to light emission following absorption of energy from an external source of light. Fluorescent emission can be from chemical or biochemical reagents. The wavelength that is emitted is longer than the wavelength that is absorbed. Specific examples of fluorescent materials include organic dyes, such as Cy-3 and Cy-5, AlexaFluor, green fluorescent protein (GFP), silicon nanoparticles, quantum dots, and a diverse collection of other materials well known in the art.

As used herein, the term "phosphorescence" refers to a phenomenon similar to fluorescence, except that the excited product is relatively more stable. Accordingly, the time until energy is released is longer compared to fluorescence, resulting in a glow after the excitation light has been removed. Phosphorescent emission also can be from a chemical or biochemical reagent.

As used herein, the term "absorbance" refers to a phenomenon wherein excitation light impinging on matter is absorbed, reduced in intensity, or transformed to a different phase, wavelength, or other property, in such a way that the said absorbance can be measured.

As used herein, the term "emission reagent" refers to luminescent, fluorescent, or phosphorescent materials. Other emission reagents include colloidal gold, colloidal silver, other colloidal metals and non-metals, quantum dots, other fluorescent and phosphorescent nanoparticles, plasmon resonant particles, grating particles, photonic crystals reagents and the like.

As used herein, the term "absorption reagent" refers to any material that causes absorbance of the excitation light.

As used herein, the term "detector" refers to a device that can convert the absorbance and/or emission light produced by the sample or absorbance and/or emission reagent to an electronic signal or image. Examples of detectors include, but are not limited to photodiodes, one-dimensional charge-coupled device (CCD) arrays, two-dimensional CCD arrays, photomultiplier tubes (PMT), position sensitive PMTs, Complementary Metal Oxide Silicon (CMOS) image arrays, spectrometers, etc. The detector can be chosen to have maximum sensitivity in the frequency region of emission light and can be provided with a filter blocking the excitation light source, ambient light or noise, or other extraneous or undesirable wavelengths. One or more detectors can be used.

The absorption and/or emission signal produced by the absorbance and/or emission reagent can be detected as total energy or as energy as a function of wavelength.

The emission signal produced by the emission reagent can be detected as energy measured at one point in time (specified duration), averaged over a period of time, measured as a reduction in intensity over a period of time (time resolved), or integrated over a period of time. For emission reagents such as quantum dots, which can remain photo stable after exposure to long periods of excitation light sources as compared to organic dyes, integration of the signal over a longer period of time than organic dyes becomes possible and can be used to improve the sensitivity of detection.

As used herein, the term "excitation light source" refers to the radiation illumination member, comprised of light source(s) and optics. For some applications, such as colloidal gold and silver, the excitation light source can be a broad-spectrum source, while in other applications the excitation light source can be a narrow spectrum source. Some samples can be better illuminated using multiple light sources. In some multiple-analyte applications, for example, with more than one fluorescent emission reagent in the same sample, some emission reagents can require one or more narrow band excitation light sources, while other emission reagents, such as quantum dots, may be illuminated by a single narrow band or broadband excitation light source for all emission wavelengths. Lenses, filters, and other optical devices may be employed to achieve the desired or optimum illumination.

Excitation light source in some exemplary embodiments of the present invention can use any light source using any of various methods known in the art. Exemplary sources include lasers, light emitting diodes (LEDs), and other narrow and broadband light sources.

Briefly, light from a laser has the property of coherence and potentially high power, narrow wavelength band, and a beam that can be turned into a wide collimated beam, a cone beam, or a fan beam with lenses. Coherence and high power provide greater power density. Narrow band is desirable for organic dye emission reagents. Any kind of laser can be used in the apparatuses and methods of the exemplary embodiments of the invention. Diode lasers are commonly available, compact and relative low cost.

LEDs produce light that is not coherent and of broader bandwidth than lasers. LEDs are relatively inexpensive and compact. In exemplary implementations, LEDs are well suited to some applications. Alternatively, an addressable multiple-element array of optical sources, such as LEDs, can be used to sequentially probe various fluorescent materials in the sample. This multiple element array of optical sources provides a particularly low cost technique, having the advantage of no moving parts, and providing more flexibility than stepped or oscillated excitation light, because LEDs or groups of LEDs would be addressable in any temporal or spatial sequence.

Broadband incoherent light sources including, for example, incandescent lamps, fluorescent lamps, xenon lamps, mercury lamps and arc lamps, are useful in the apparatuses of the exemplary embodiments of the invention. For example, broadband ultraviolet (UV) sources can be useful for illuminating quantum dots.

A wide variety of excitation light source configurations are possible for use in the radiation illumination member. The selection among alternatives will depend, in part, on the emission reagent and the sample.

In certain exemplary embodiments of the invention, the temporal mode of radiation illumination and radiation detection can include, for example, a variety of methods and variations. Exemplary implementations include instantaneous signal, time averaged instantaneous signal, time integrated partial signal, time resolved signal, time integrated continuous whole signal, frequency modulated signals, or other variations or combinations thereof. The temporal mode of illumination and detection is related to the method of spatial illumination of the excitation light, the fluorescent emission reagent, the waveguide geometry, the number of analytes to be detected, the concentration level of the analyte, and the desired sensitivity of the detection.

Excitation light source can impinge on the absorption and/or emission reagent of the sample during the entire period of detection of each analyte. The excitation light source can be modulated or "chopped" to reduce interference from ambient light. Demodulation of the resulting emitted signal, such as with a lock-in amplifier, can then reduce background interference. Such modulation may not be required, if ambient light is eliminated by optical isolation or shielding.

According to an exemplary implementation, a method of illumination is for the excitation light source to emanate from a wide or diffused area, and to illuminate the entire sample from one or more directions. Advantages of this unfocused or diffused illumination method include, for example: (1) illuminating substantially the entire sample, and (2) minimizing alignment procedures, since the illumination areas may be larger than the sample size.

One or more excitation light sources can be used sequentially or simultaneously to provide different illumination wavelengths and/or to provide different spatial and temporal coverage. The angle of incidence of the excitation light can be perpendicular to the incident surface(s) of the flow through waveguide, perpendicular to the length of the flow through waveguide, or at one or more angles in relation to the surface (s) of the flow through waveguide. The optimal angle of illumination can be selected so as to reduce the background noise resulting from excitation light or to enhance any other desirable characteristics of the device. The excitation light can be collimated, non-collimated, point source, from multiple point sources, diffused source or broad area unfocused source. The angle of illumination need not be limited to excitation perpendicular to the surface of the flow through waveguide.

An optimal angle of illumination is dependent on the size and shape of the flow through waveguide and the desired detection limit. A long flow through waveguide can reduce collected excitation light at the detector, because each time the excitation light reflects on a boundary of the waveguide, part of the excitation light is lost due to transmission out of the waveguide.

One aspect of certain exemplary embodiments of the present invention is to provide a sensitive luminescence detection system comprising an instrument and a flow through waveguide to hold the sample. The flow through waveguide is efficient in gathering the luminescent emission light and guiding the light to the detector.

Another aspect of certain exemplary embodiments of the invention is a system that includes an excitation light source and a sensitive detection system to detect the change of both the excitation and emission signals from samples in a flow through waveguide. As stated above, the flow through waveguide is efficient in gathering the emission light and guiding it to the detector. The flow through waveguide design, the arrangement of the excitation light illumination, and optical filters may be configured to facilitate detection of very low concentrations of absorption and/or emission reagents and for ease of use.

To achieve at least some of the foregoing aspects of the exemplary embodiments for luminescence applications, a luminometer is provided comprising a flow through waveguide and one or more detectors. The flow through waveguide may include a hollow region to hold the sample. The flow through waveguide can be made of material that guides emission light to the closed end of the flow through waveguide. The instrument can include a device to introduce the sample and reagents into the flow through waveguide. One or more detectors may be provided that detect the emission light from the flow through waveguide.

Also, to achieve at least some of the foregoing objects of the exemplary embodiments for fluorescence and absorbance applications, a fluorometer or photometer is provided that comprises a flow through waveguide, one or more excitation light sources and one or more optical detectors. The flow through waveguide has a hollow region to hold the sample. The excitation light is introduced at an angle or perpendicular to one surface of the flow through waveguide. The flow through waveguide is made of material that can guide emission light to the closed end of the flow through waveguide. There can be one or more detectors that detect the emission light coming out of the closed end of the flow through waveguide.

DETAILED DESCRIPTION OF EXEMPLARY EMBODIMENTS

In an exemplary embodiment, as shown in FIGS. 1-13 and 15-16, for fluorescence and absorbance applications, a fluorometer/photometer is provided that comprises one or more flow through waveguides, one or more lens attachments to the flow through waveguides, one or more optical systems, one more excitation light sources and one or more optical detectors.

Figure 1:
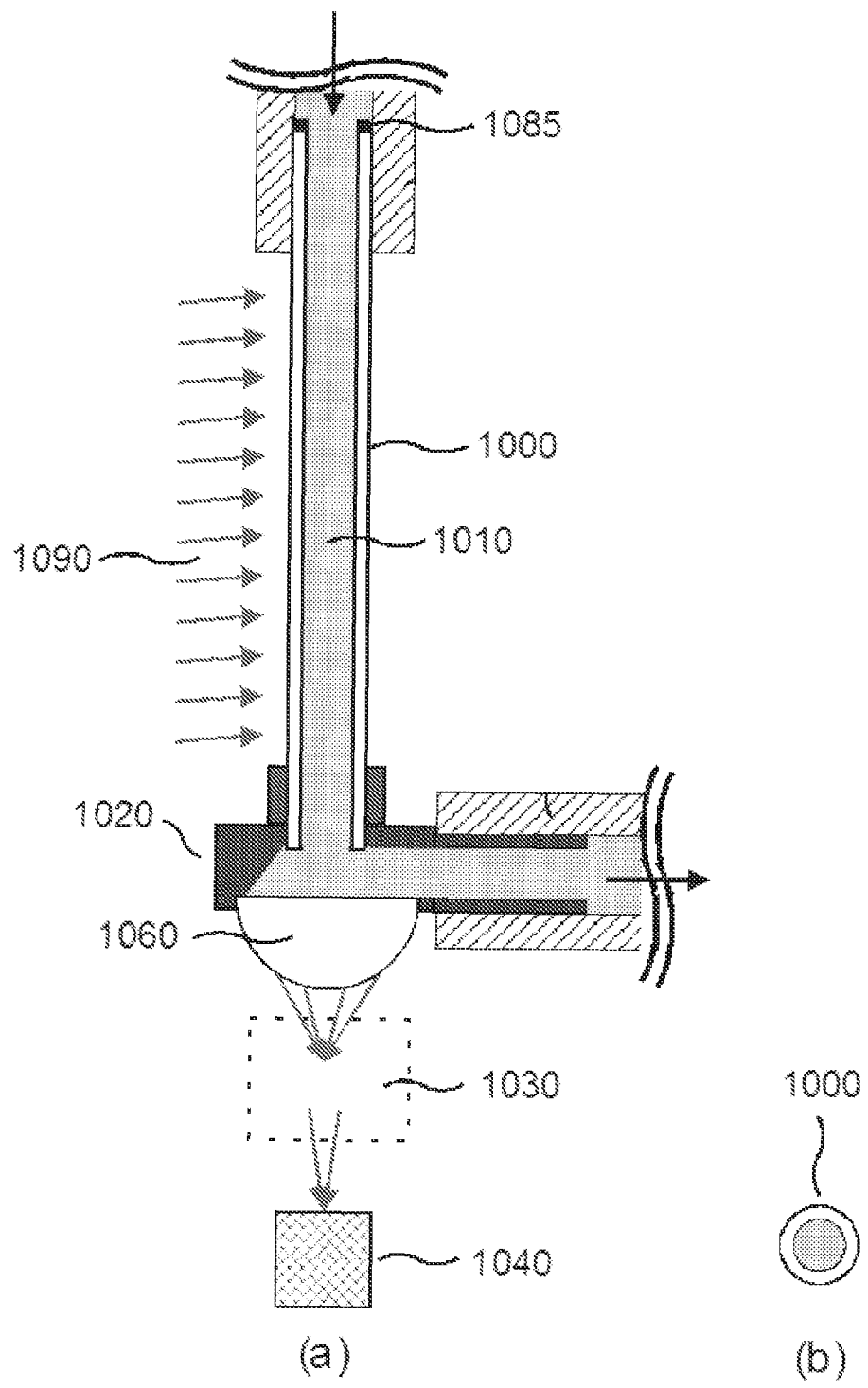
FIG. 1. (a) Schematic side view of fluorescence/absorbance flow through detection system according to an exemplary embodiment of the present invention, where the flow through waveguide with the same cross sectional shape along the long axis. (b) Cross sectional view of the flow through waveguide.

Referring to FIG. 1, The sample enters from one end of the waveguide and exits from the other end. A focusing lens is attached to one end of the flow through waveguide via a lens attachment to focus the emission light, passing through optical elements to a detector. There is a light source and optics to form the desired pattern, intensity, and wavelength of the light. That is, in FIG. 1, the sample 1010 enters the flow through waveguide 1000 from one end and exits from the other end. The excitation light 1090 is introduced at an angle nearly perpendicular to one surface of the flow through waveguide 1000. The flow through waveguide 1000 is made of material that can guide emission light to the end of the flow through waveguide with a lens 1060. There are one or more detectors 1040 that detect the absorption and/or emission light coming out of the flow through waveguide 1000. Schematic of flow through waveguide 2000 with cylindrical wall is shown in FIG. 1b.

The waveguide assembly, according to an exemplary implementation includes the waveguide 1000, the connector 1020 and the lens 1060. In yet another exemplary implementation, to increase the signal, the end of the waveguide away from the lens 1085 is coated with a reflective material 1085 (see also exemplary applications of reflective material 2085 of FIG. 2, as well as 9085, 10085, 11085, 12085, 15085, 19085, 21085, 22085, 23085, 25075 and 26085 in FIGS. 9-12, 15, 19-23 and 25, respectively).

The excitation light 1090 is incident nearly perpendicular to the surface of the flow through waveguide 1000, but with a slight tilt towards the end of the flow through waveguide without a lens.

There is a set of optical elements between the excitation light source and the flow through waveguide 1000 to filter the excitation light, and form the shape of the excitation light and direct the excitation light to the flow through waveguide.

There can be a set of optical elements 1030 to focus, guide or filter the absorption and/or emission light.

The detector 1040 can be one of the following: spectrometer, PMT, CCD, CMOS imaging arrays or photodiode, or any other optical detector. The detection of signal can be gathered once or repeatedly over the specified duration of the sample flow.

The applications may comprise the following arrangements and design alternatives.

Figure 2:
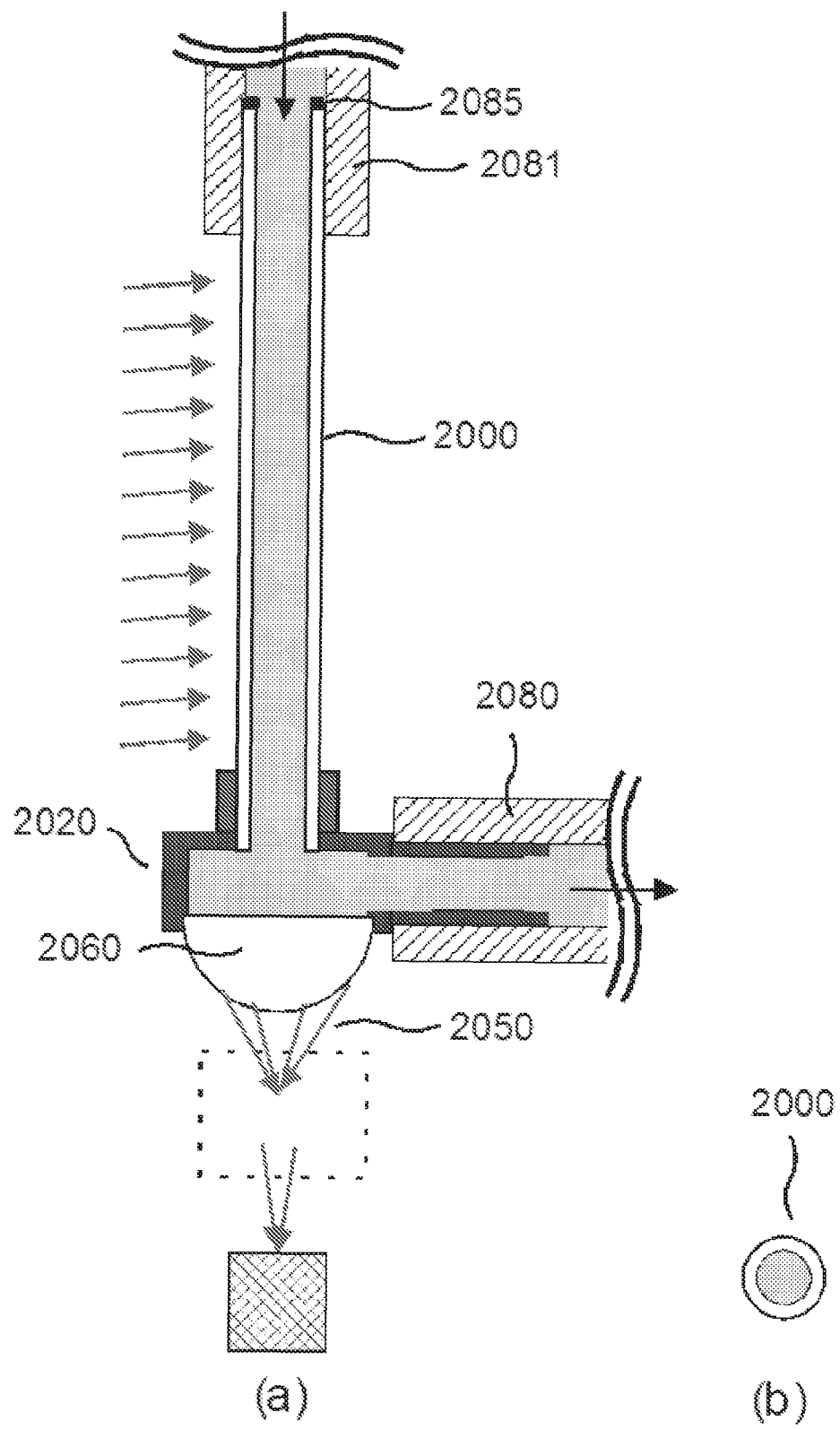
FIG. 2. Schematic side view of fluorescence/absorbance flow through detection system according to an exemplary embodiment of the present invention that may be similar to FIG. 1 and includes a lens attachment.

A flow through waveguide 2000 with a different lens attachment 2020 is shown in FIG. 2. Any lens attachment that locates the lens to the flow through waveguide at the correct place and allows appropriate flow would be applicable.

Figure 3:
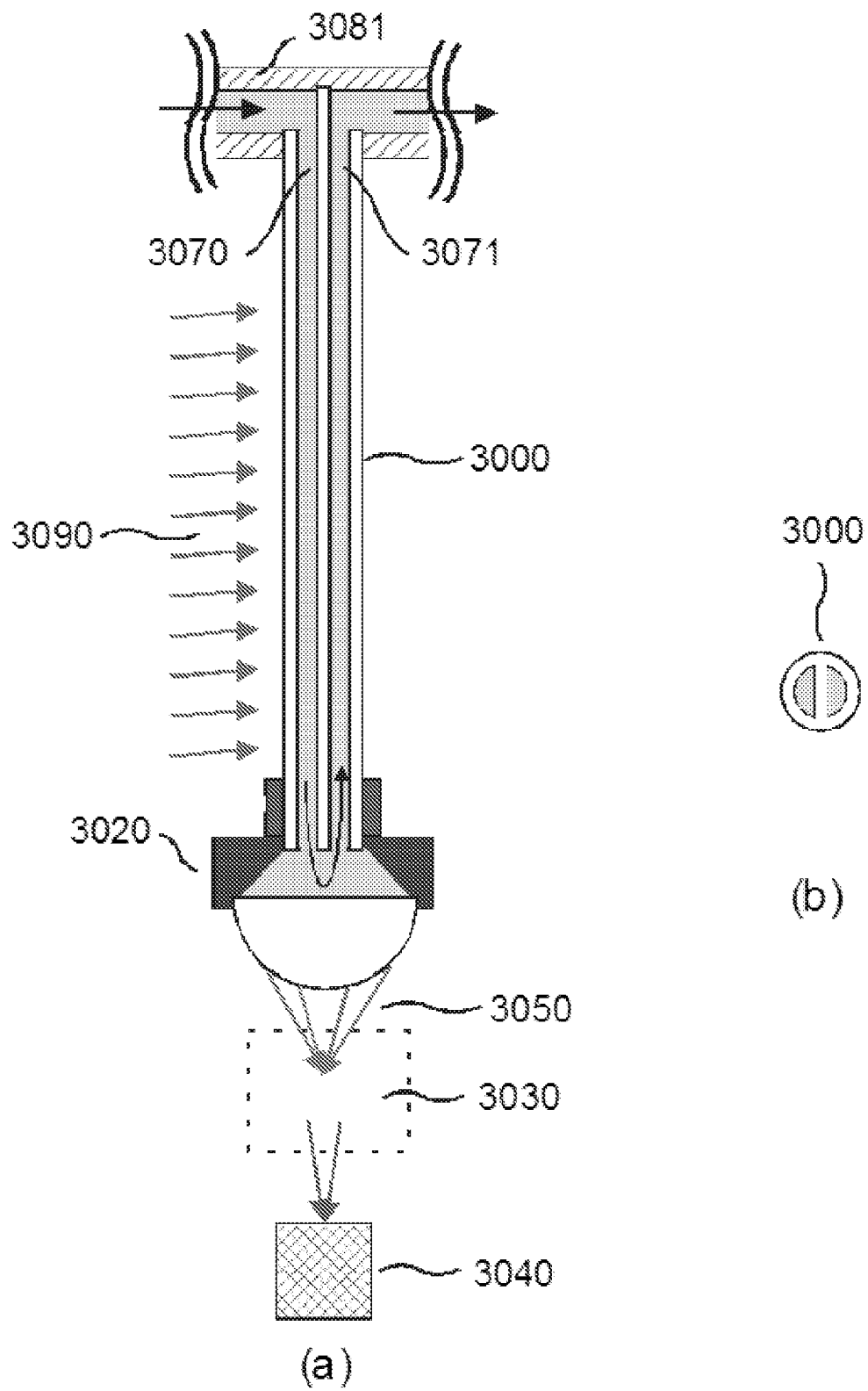
FIG. 3. (a) Schematic side view of fluorescence/absorbance flow through detection system according to an exemplary embodiment of the present invention, where the flow through waveguide with the same cross sectional shape along the long axis. (b) Cross sectional view of the flow through waveguide.

Referring to FIG. 3, Sample enters from end of first one of two flow through channels of the waveguide. The first channel ends at the other end of the waveguide and the sample flow returns into the second channel of the waveguide and exits from the same end of the waveguide as it enters. A focusing lens is attached to one end of the flow through waveguide via a lens attachment to focus the emission light, passing through optical elements to a detector. There is a light source and optics to form the light. The flow through waveguide can have two channels 3070 and 3071, as shown in FIG. 3. Sample enters the first channel 3070 of the distal end of the flow through waveguide via connector 3081. At the proximal end of the flow through waveguide, the sample returns into the second channel of the waveguide 3071 and exits from the distal end. A focusing lens is attached to the proximal end of the flow through waveguide via a lens attachment 3020 to focus the absorption and/or emission light 3050, passing through optical elements 3030 to a detector 3040. There is a light source and optics to form the excitation light 3090. The cross sectional view of the flow through waveguide 3000 showing two channels is shown in FIG. 3b.

Figure 4:
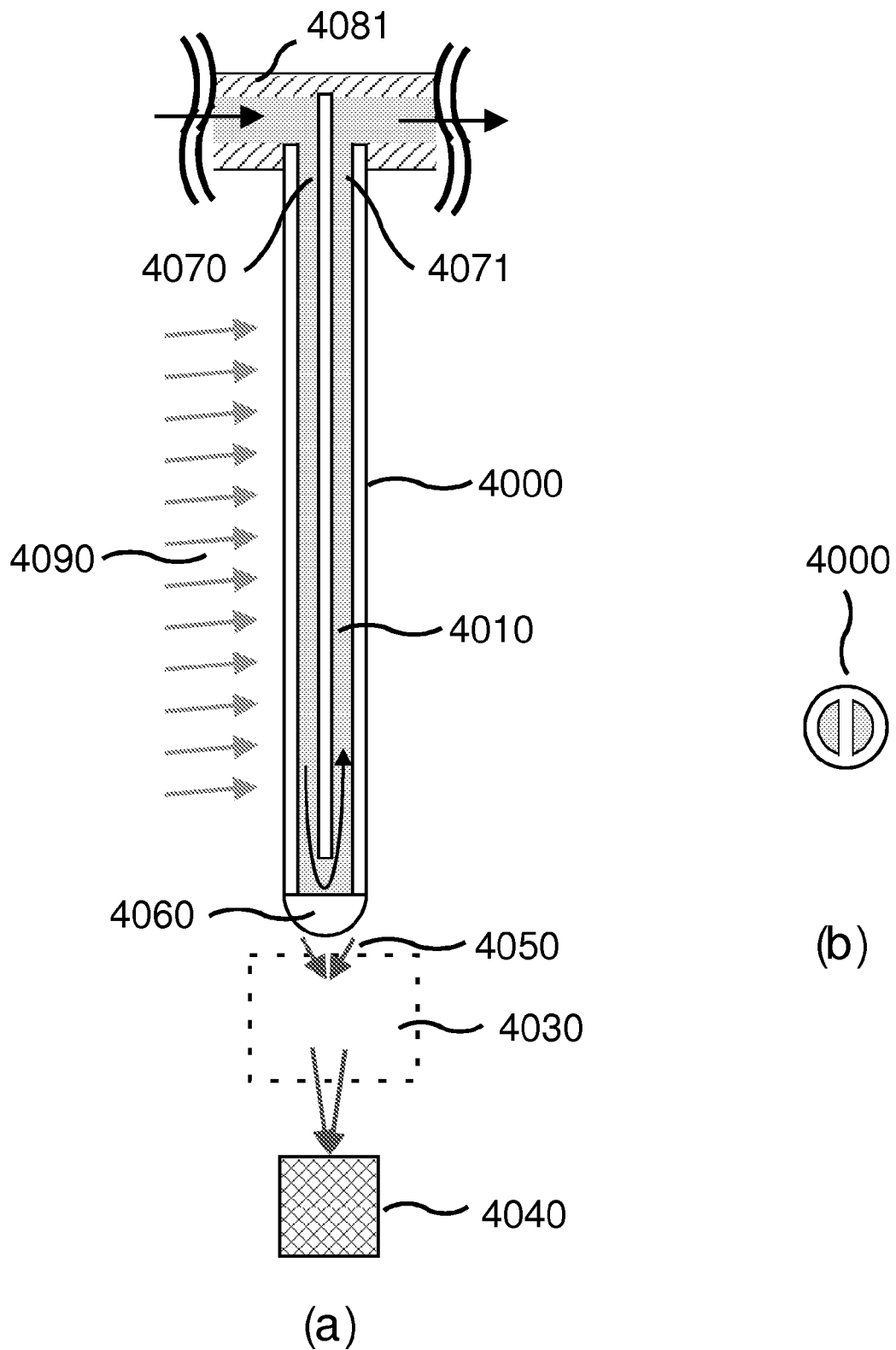
FIG. 4. (a) Schematic side view of fluorescence/absorbance flow through detection system according to an exemplary embodiment of the present invention, where the flow through waveguide has the same cross sectional shape along the long axis. (b) Cross sectional view of the flow through waveguide.

Referring to FIG. 4, Sample enters from one end of the first of two flow through channels of the waveguide. The first channel ends at the other end of the waveguide, where the sample flow returns into the second channel of the waveguide and exits from the same end of the waveguide as it enters. A focusing lens is directly attached to the end of the flow through waveguide where the sample turns to focus the emission light, passing through optical elements to a detector. There is a light source and optics to form the light. The flow through waveguide can have two channels, as shown in FIG. 4. Sample enters the first channel 4070 of the distal end of the flow through waveguide via connector 4081. At the proximal end of the flow through waveguide, the sample returns into the second channel of the waveguide 4071 and exits from the distal end. A focusing lens 4060 is directly attached to the proximal end of the flow through waveguide. Absorption and/or emission light 4050 exiting the lens 4060 passes through optical elements 4030 to a detector 4040. There is a light source and optics to form the excitation light 4090. The cross sectional view of the flow through waveguide showing two channels 4000 is shown in FIG. 4b.

Figure 5:
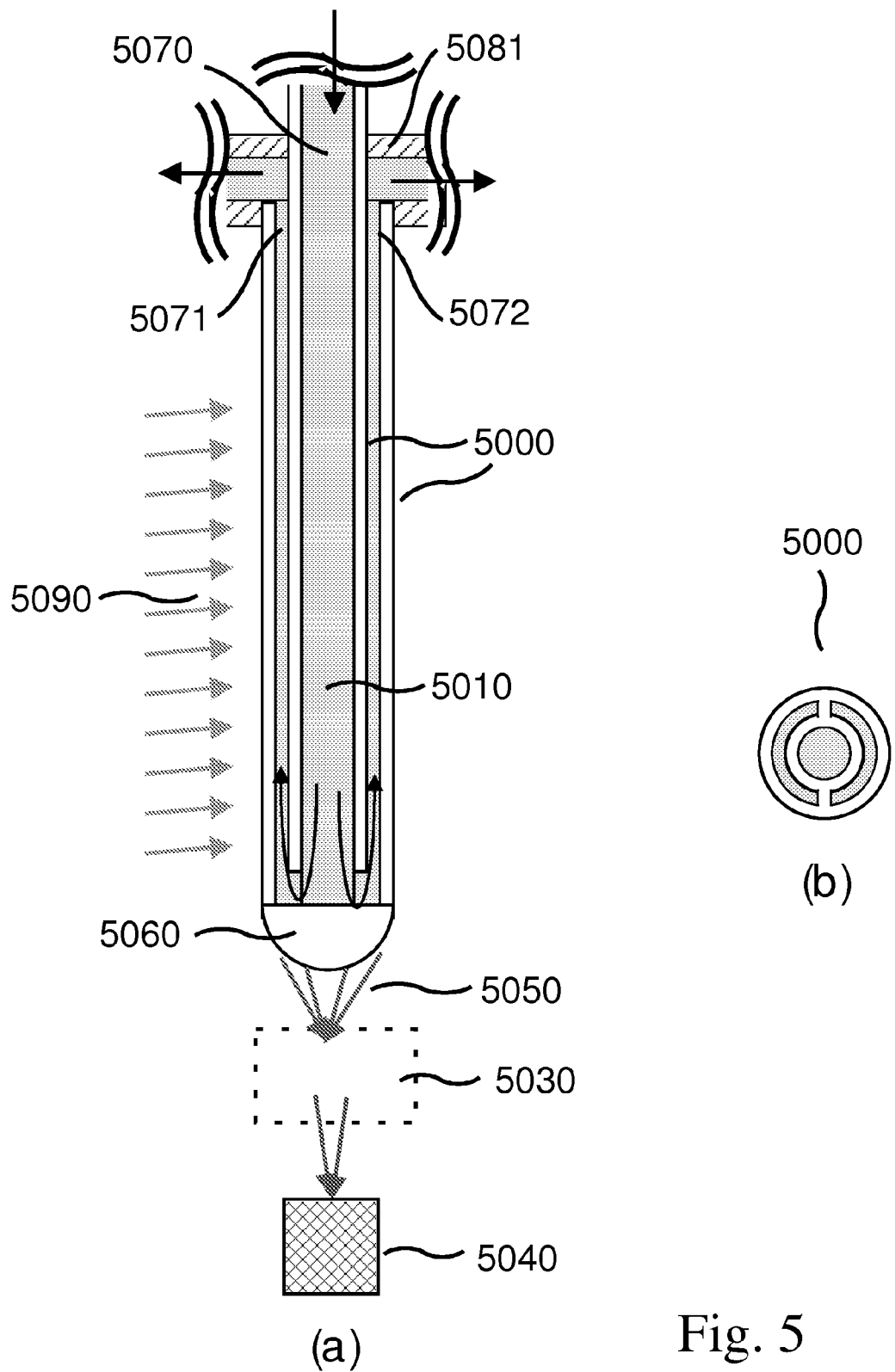
FIG. 5. (a) Schematic side view of fluorescence/absorbance flow through detection system according to an exemplary embodiment of the present invention, where the flow through waveguide has the same cross sectional shape along the long axis. (b) Cross sectional view of the flow through waveguide.

Referring to FIG. 5, Sample enters from one end of first of three flow through channels of the waveguide. The first channel ends at the other end of the waveguide, where the sample flow returns into the second and third channels of the waveguide and exits from the same end of the waveguide as it enters. A focusing lens is directly attached to the end of the flow through waveguide where the sample turns to focus the emission light, passing through optical elements to a detector. There is a light source and optics to form the light. The flow through waveguide can have more than two channels 5070 and 5071 and 5072, as shown in FIG. 5a. Sample enters the first channel 5070 of the distal end of the flow through waveguide via connector 5081. At the proximal end of the flow through waveguide, the sample 5010 returns into the second and third channels of the waveguide 5071 and exits from the distal end. A focusing lens 5060 is attached to proximal end of the flow through waveguide 5000 via a lens attachment 3020 to focus the absorption and/or emission light 5050, passing through optical elements 5030 to a detector 5040. There is a light source and optics to form the excitation light 5090. The cross sectional view of the flow through waveguide 5000 showing three channels is shown in FIG. 3b.

Figure 6:
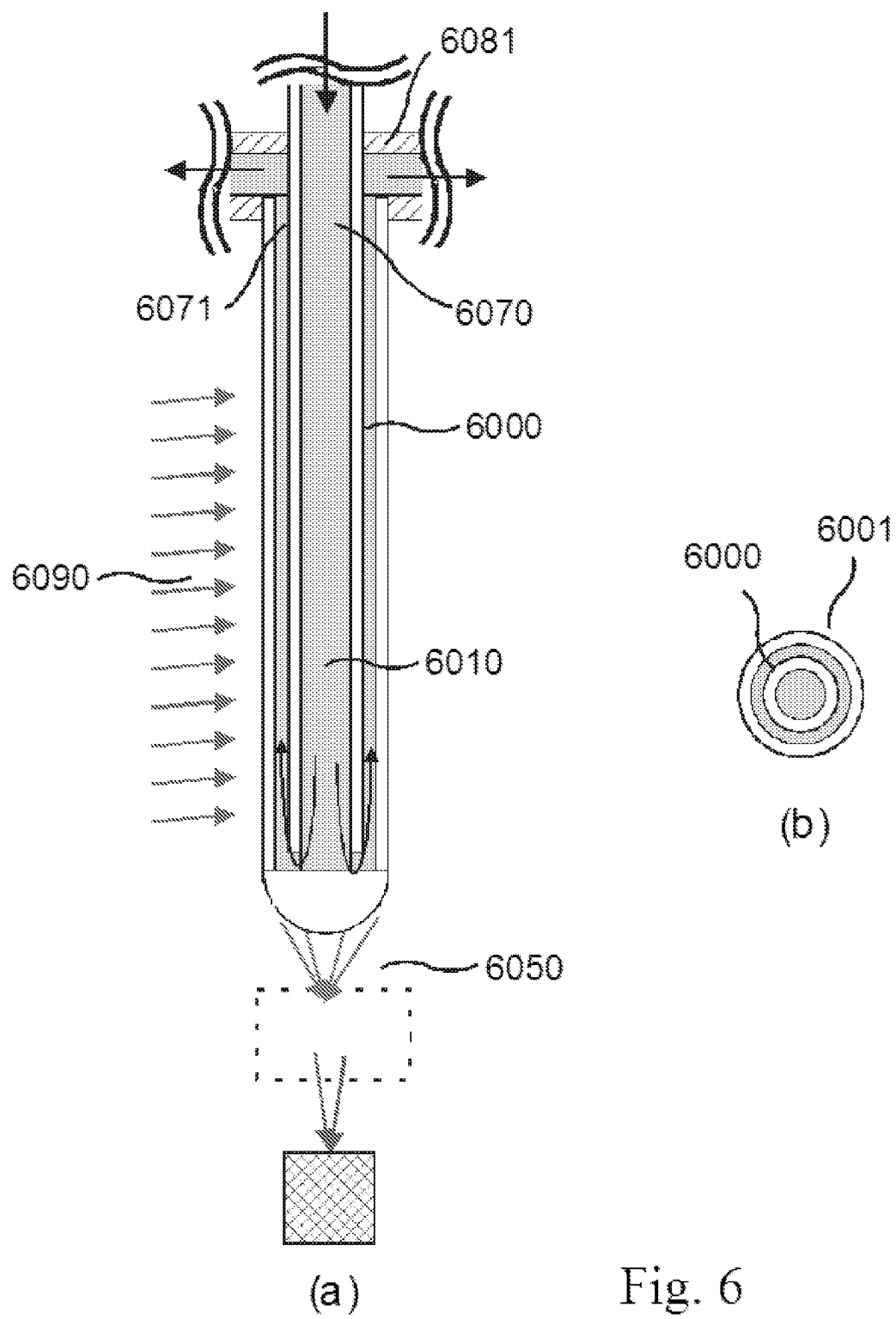
FIG. 6. (a) Schematic side view of fluorescence/absorbance flow through detection system according to an exemplary embodiment of the present invention, where the flow through waveguide has the same cross sectional shape along the long axis. (b) Cross sectional view of the flow through waveguides. The inner and outer channels of the flow through waveguide are not connected.

Referring to FIG. 6, Sample enters from one end of first of two flow through channels of the waveguide. The first channel ends at the other end of the waveguide, where the sample flow returns into the second channel of the waveguide and exits from the same end of the waveguide as it enters. A focusing lens is directly attached end of the flow through waveguide where the sample turns to focus the emission light, passing through optical elements to a detector. There is a light source and optics to form the light. Schematic side view of fluorescence/absorbance flow through detection system, where the flow through waveguide utilizes two concentric channels is shown in FIG. 6. Sample enters the first channel 6070 of the distal end of the flow through waveguide via connector 6081. At the proximal end of the flow through waveguide, the sample 6010 returns into the second and third channels of the waveguide 6071 and exits from the distal end. A focusing lens is directly attached to the proximal end of the flow through waveguide where the sample turns to focus the absorption and/or emission light, passing through optical elements to a detector. There is a light source and optics to form the excitation light 6090. The cross sectional view of the flow through waveguide showing two channels is shown in FIG. 6b. The inner and outer channels of the flow through waveguide may or may not be connected at various points along the length of the flow through waveguide.

Figure 7:
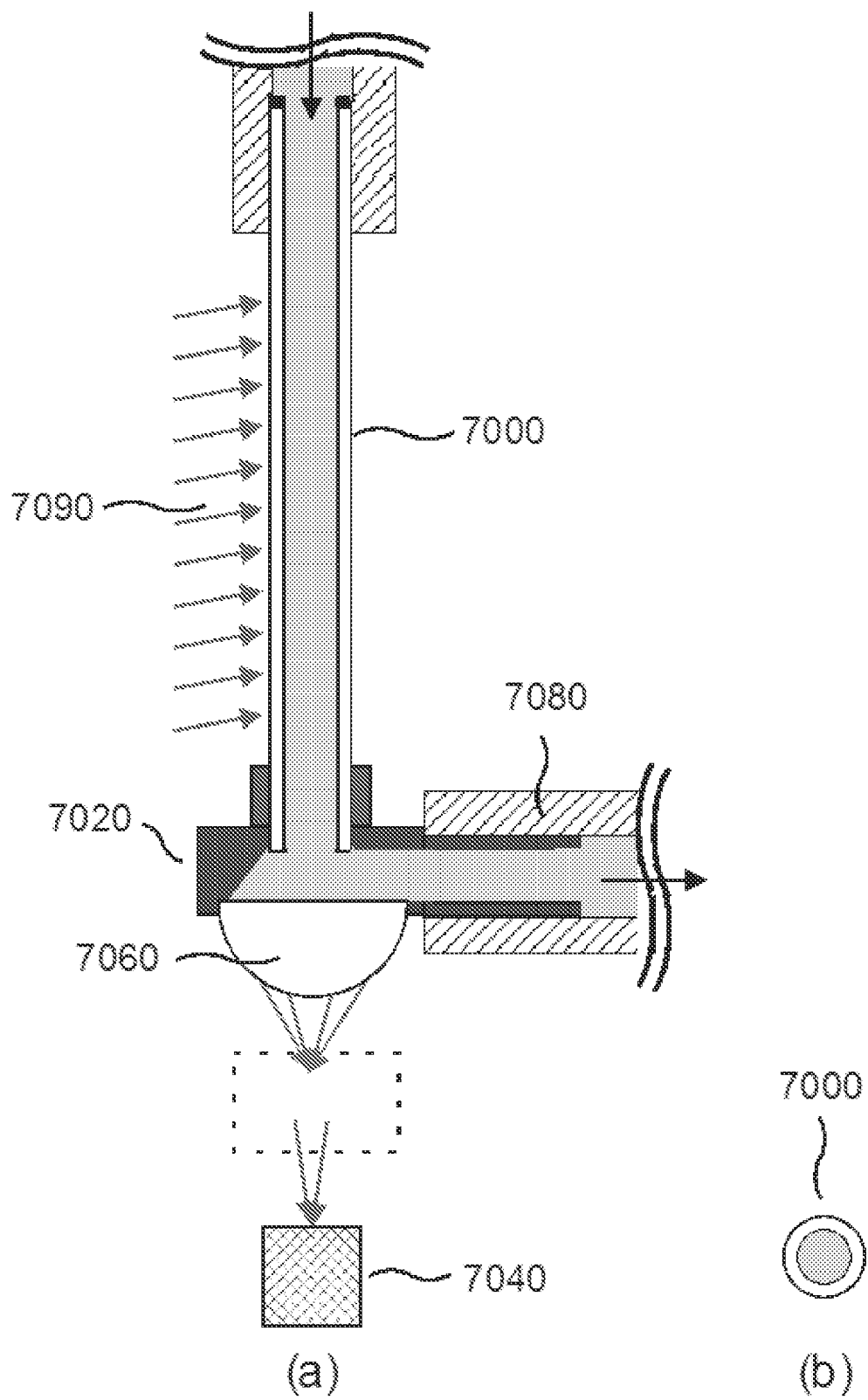
FIG. 7. Schematic side view of fluorescence/absorbance flow through detection system according to an exemplary embodiment of the present invention, where the angle of the excitation light angle may be varied to minimize the excitation light entering the detector.

The excitation light 7090 can be nearly perpendicular or impinge at any angle to the surface of the flow through waveguide, as shown in FIG. 7.

Figure 8:
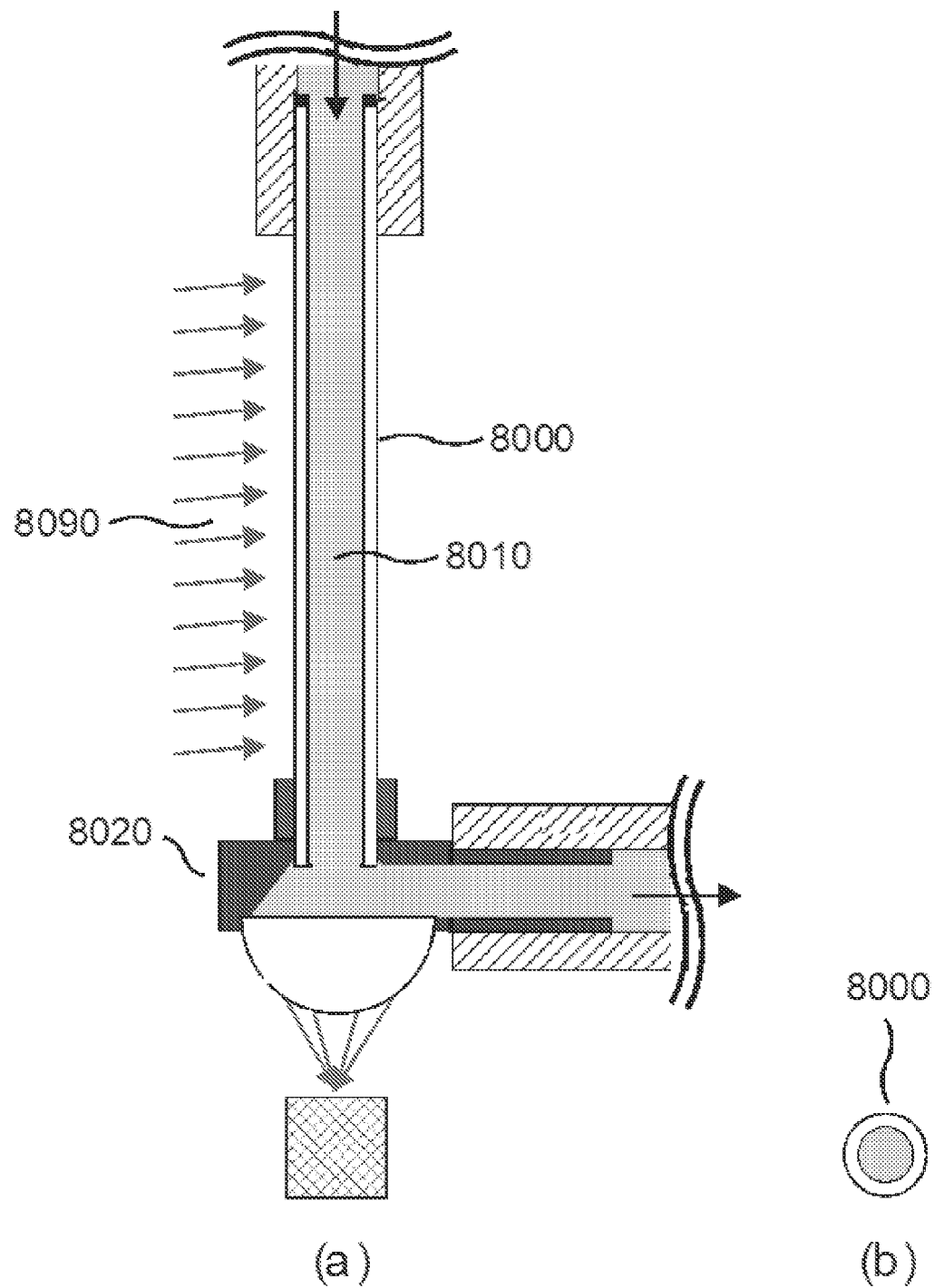
FIG. 8. Schematic side view of fluorescence/absorbance flow through detection system according to an exemplary embodiment of the present invention, where there are no optical elements between the flow through waveguide and the detector.

There may be no optical elements between the flow through waveguide 7000 and the detector 7060, as shown in FIG. 8.

Figure 9:
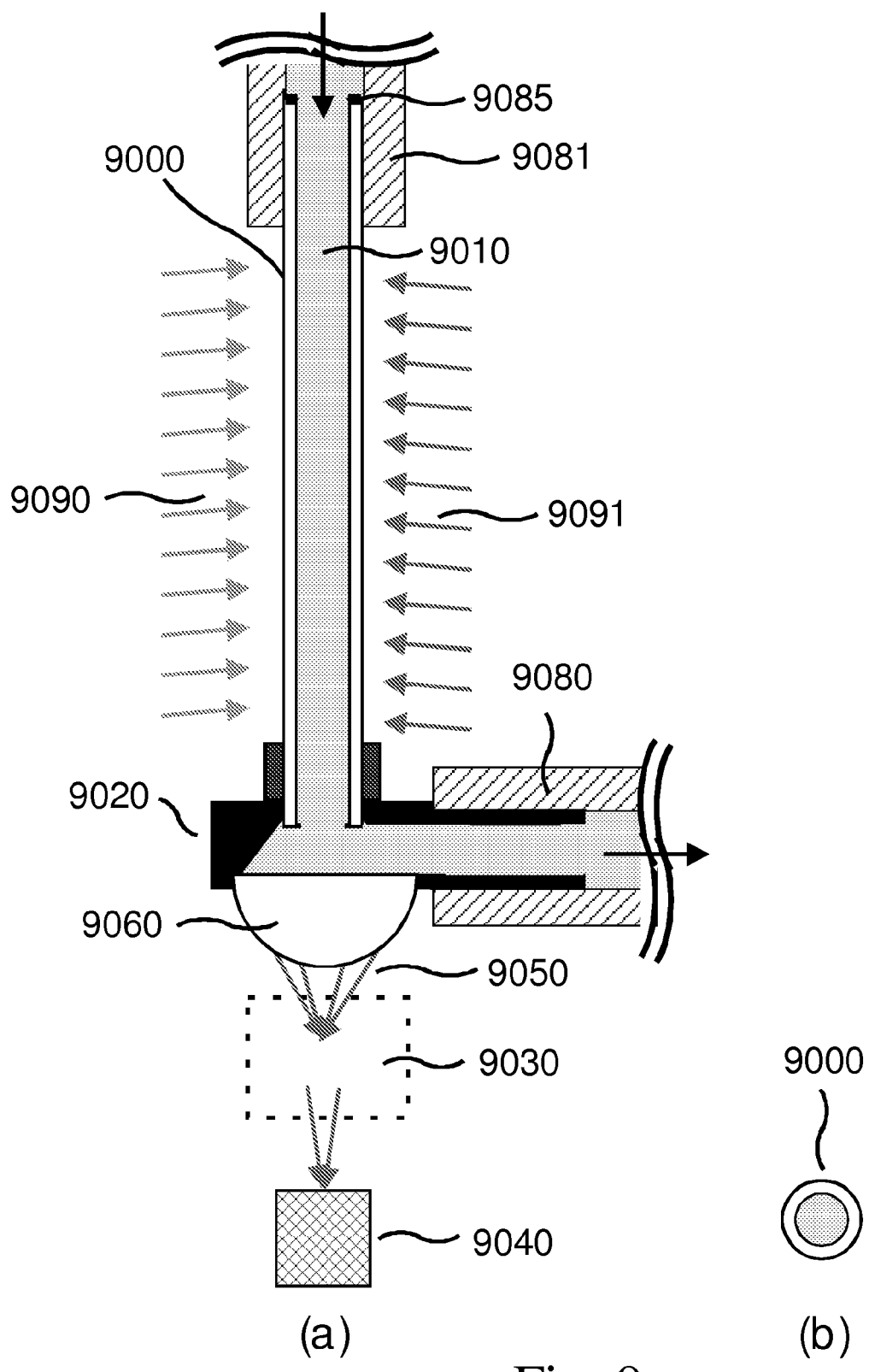
FIG. 9. Schematic side view of fluorescence/absorbance flow through detection system according to an exemplary embodiment of the present invention, where two or more excitation light sources are used to excite the sample from different directions.

There can be one or more excitation light sources 9090 and 9091, as shown in FIG. 9.

Figure 10:
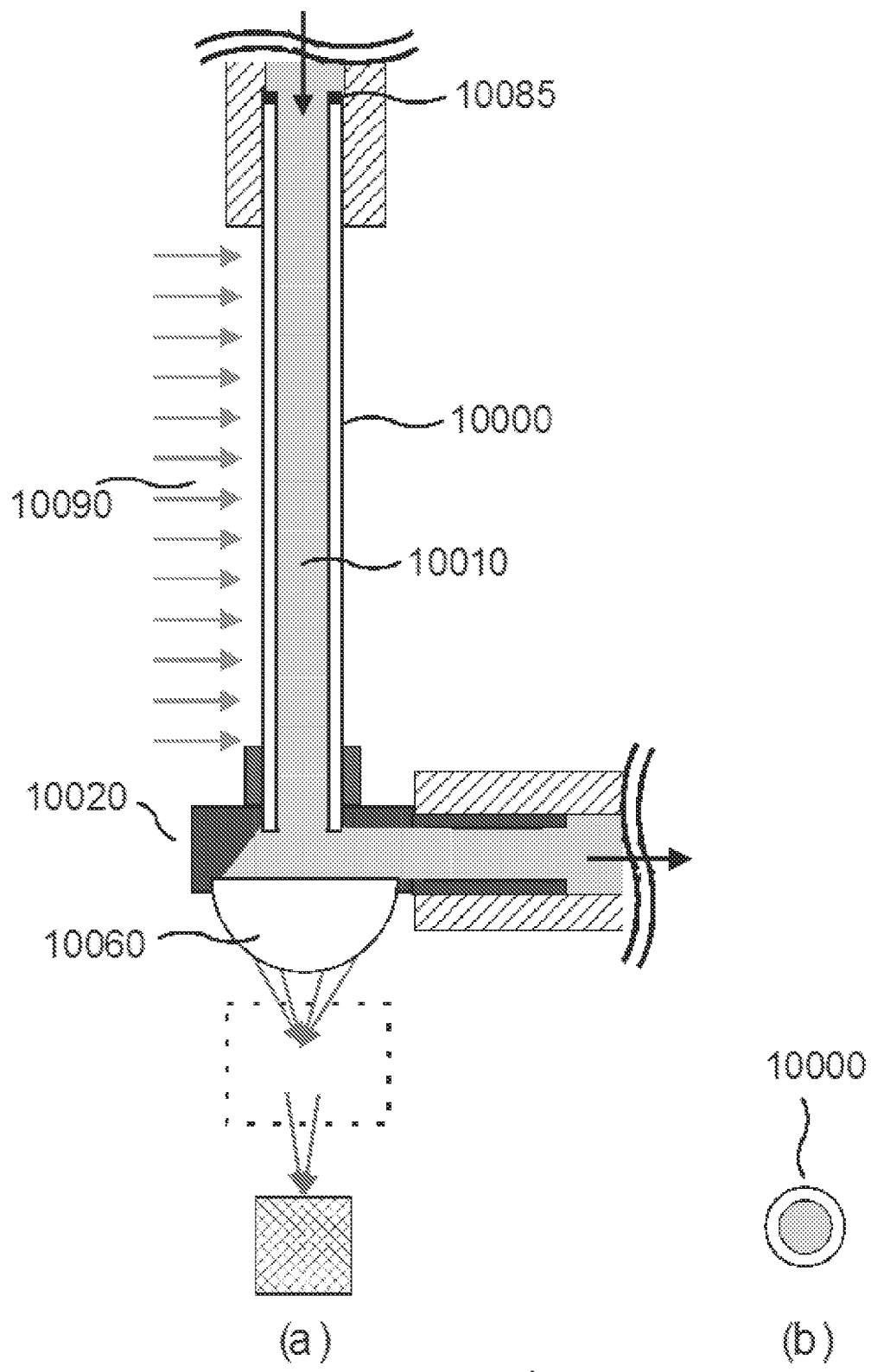
FIG. 10. Schematic side view of fluorescence/absorbance flow through detection system according to an exemplary embodiment of the present invention, where the excitation light source is perpendicular to the surface of the flow through waveguide.

The excitation light may be perpendicular to the surface(s) of the flow through waveguide, as shown in FIG. 10.

Figure 11:
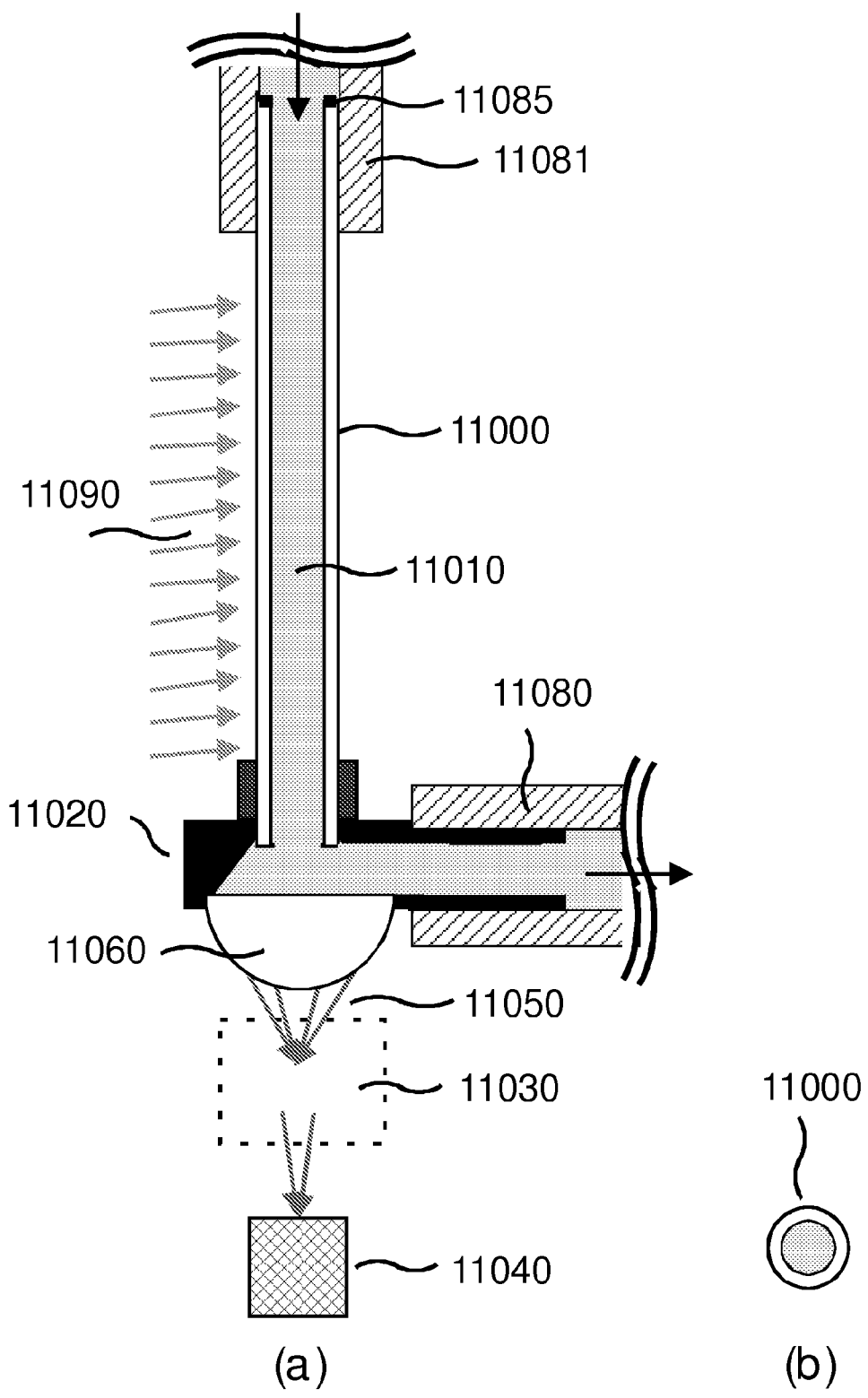
FIG. 11. Schematic side view of fluorescence/absorbance flow through detection system according to an exemplary embodiment of the present invention, where the excitation light source is not collimated and needs not be perpendicular to the surface of the flow through waveguide.

The excitation light need not be parallel collimated, as shown in FIG. 11.

Figure 12:
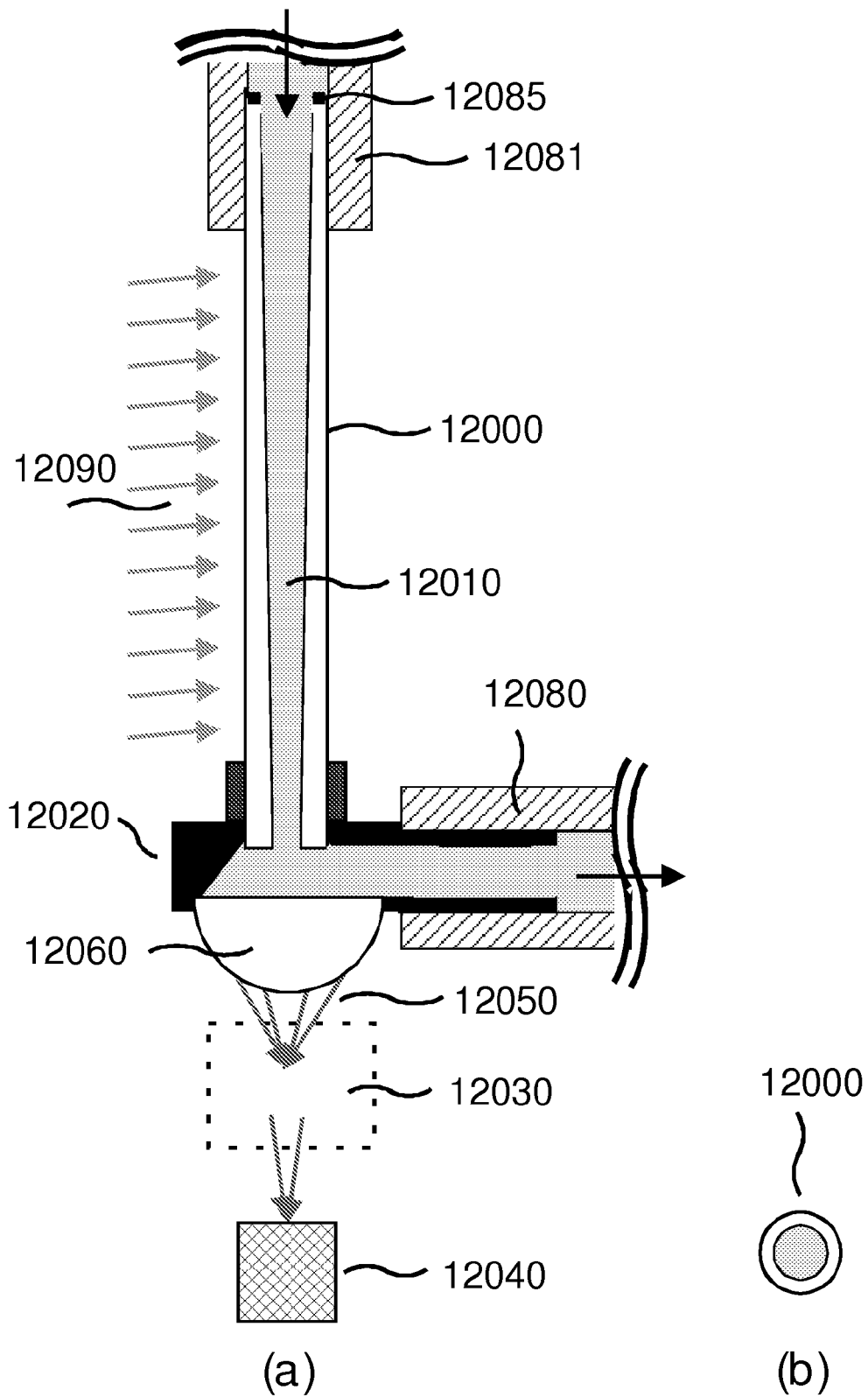
FIG. 12. Schematic of the flow through waveguide according to an exemplary embodiment of the present invention, where the axial dimensions is allowed to vary.
Figure 13:
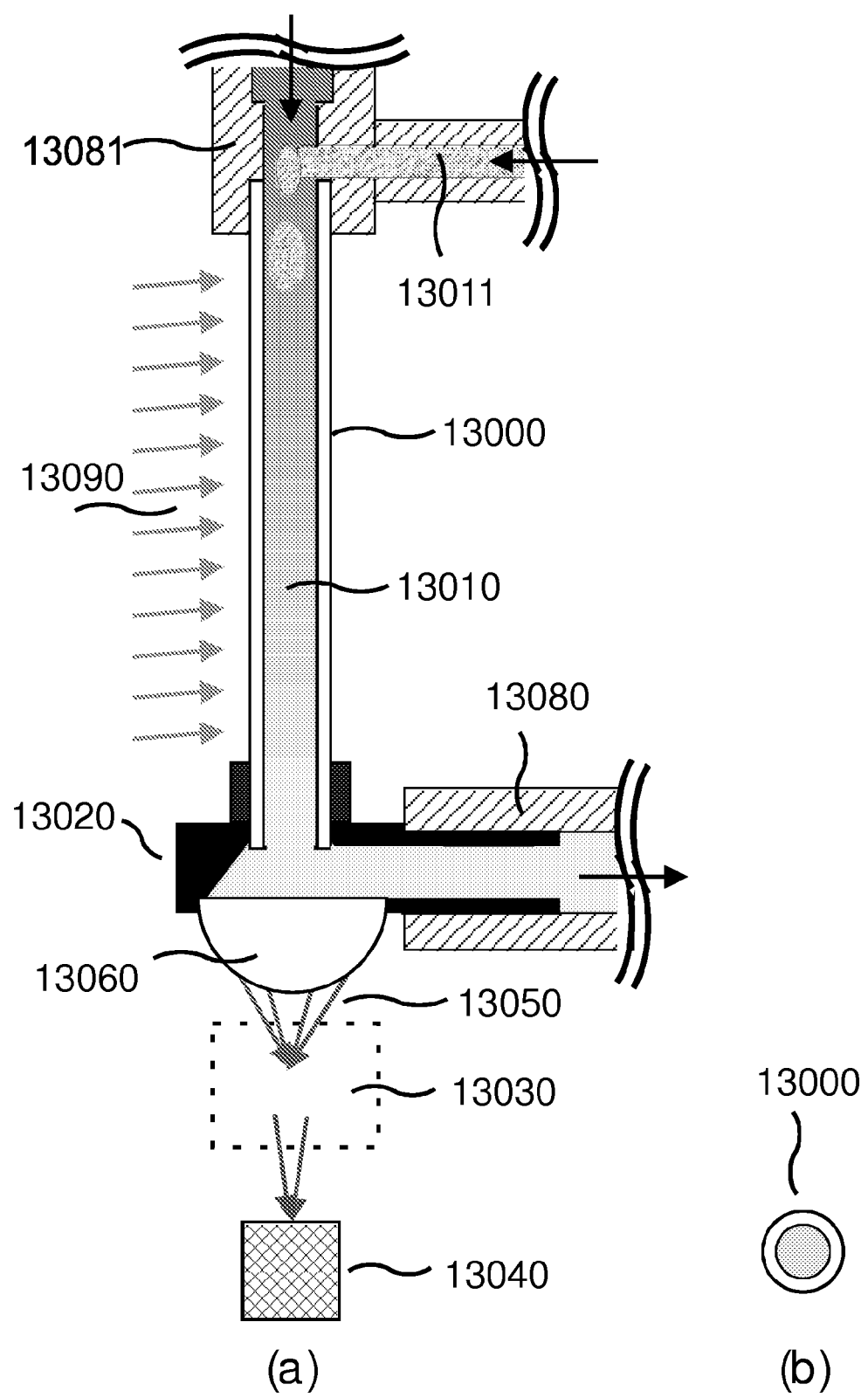
FIG. 13. Schematic side view of fluorescence/absorbance flow through detection system according to an exemplary embodiment of the present invention, where there is a inlet for reagent or second sample.

Along the length of the flow through waveguide, parts of the boundaries can be uniform and part can be varying, as shown in FIG. 12.

The material that flows into the flow through waveguide is not limited to just one sample. The connector 13081 to the flow through waveguide can allow additional reagents or samples to enter the flow through waveguide with appropriate switching of valves. The addition of reagents, for example, can cause a chemical reaction, as indicated by change of gray scale in FIG. 13.

Figure 14:
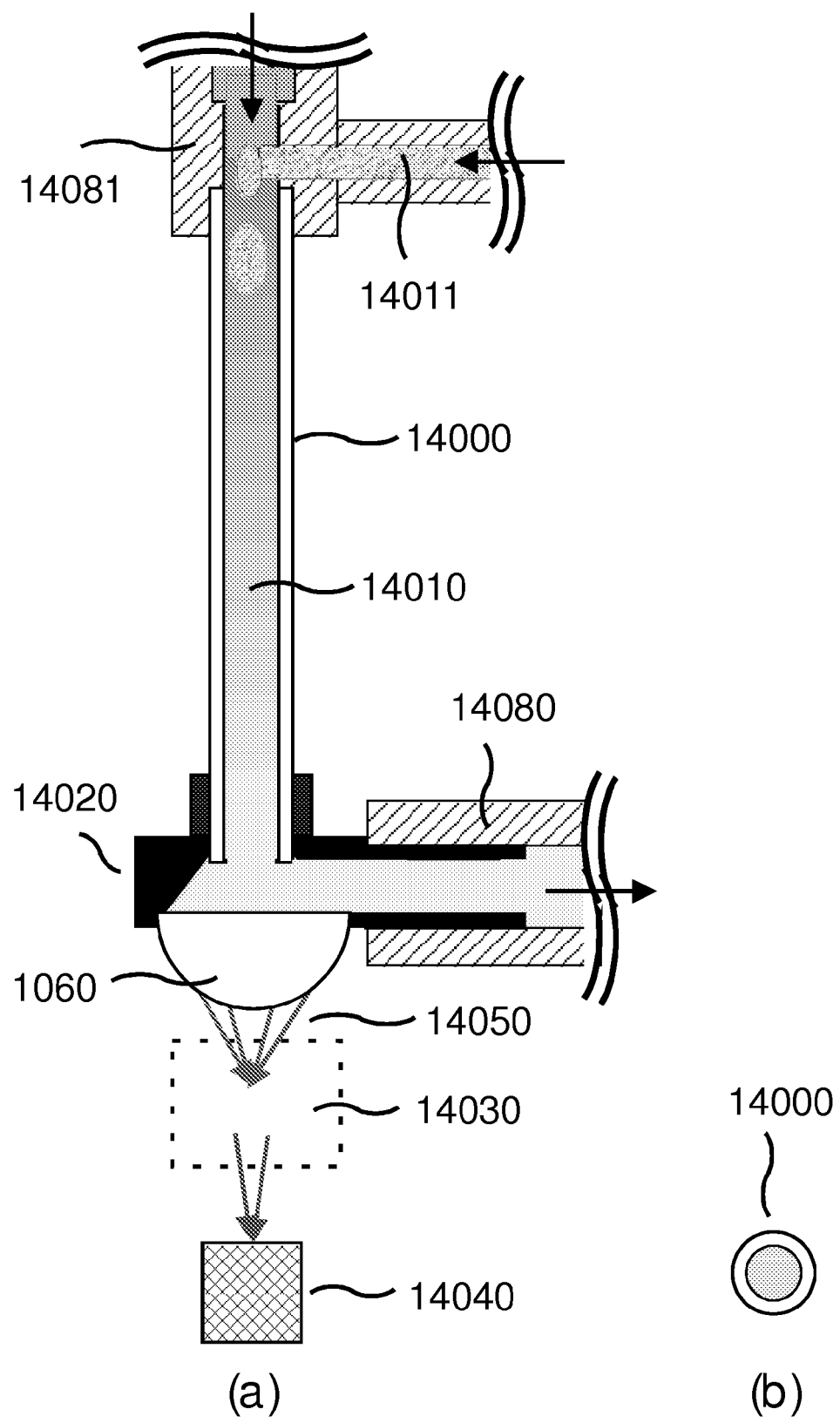
FIG. 14. Schematic side view of luminescent flow through detection system according to an exemplary embodiment of the present invention, where there is no excitation light source.

If the chemical reaction caused by the addition of reagent can produce emission signal 15080 such as luminescence, the signal can be detected without the use of excitation light source, as shown in FIG. 14.

Figure 15:
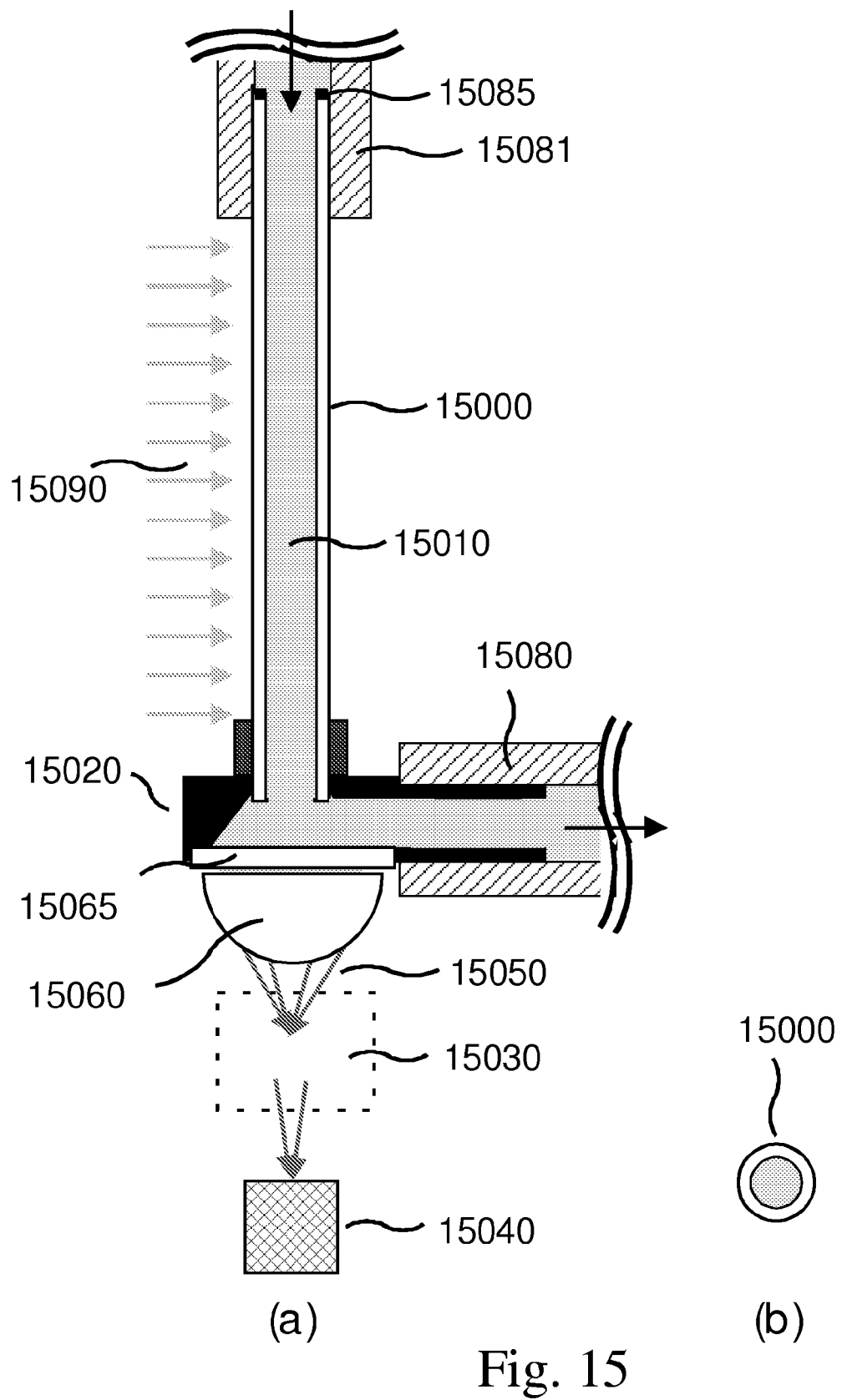
FIG. 15. Schematic of another exemplary implementation of an embodiment of the present invention where the lens is separate from the waveguide assembly, and a clear material forms a portion of the connector FIG. 16. Schematic of another exemplary implementation of an embodiment of the present invention where a clear material forms essentially the whole connector.

FIG. 15 shows an embodiment where the waveguide assembly does not include a lens, and a flat clear material 15065 is used. Lens 15060 used in this exemplary implementation is not attached to, nor need be integrally formed with, the waveguide assembly.

Figure 16:
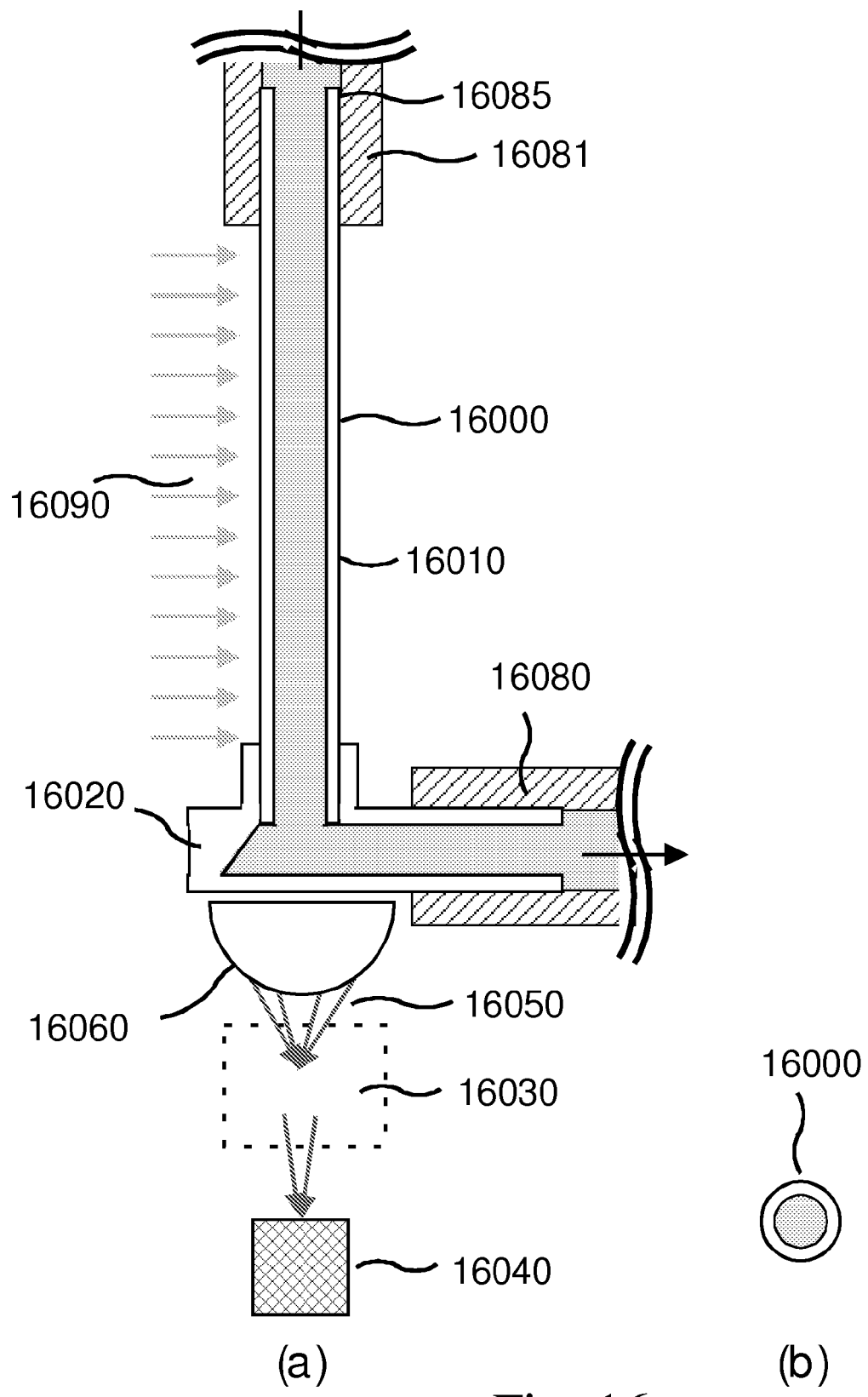

According to another embodiment as illustrated in FIG. 16, the connector 16020 is made of clear material as one piece rather then a two-piece configuration (15020 and 15065) shown in the example of FIG. 15. Similarly, according to yet another embodiment, the connector 10020 and the lens 10060

(as illustrated in FIG. 10) can be made as a one piece configuration (not shown) using the same clear material.

In addition to the input sample, more than one reagent and/or other samples can be configured to flow into any of the flow through waveguides.

The direction of flow in all the figures can be reversed.

Various cross-sectional shapes of the flow through waveguide and of the sample area are possible, as long as they are efficient in guiding the absorption and/or emission signal. The cross-sectional shapes of the outer surface(s) of the flow through waveguide can have one shape, round for example, and the cross-sectional shape of the sample area can have a different shape, square for example.

The number of flow through channels is not limited to 1, 2 or 3.

On the end of flow through waveguide that sample flow in, there can be one or more valves to introduce reagents, chemicals or additional samples.

The flow through waveguide can be made of any high index of refraction material, such as glass, plastic, etc.

The index of refraction at different parts of the waveguide can be varied. For example, a coating or coatings may be made on the outside surface of the flow through waveguide, such as acrylate, silicon/PFA, polyimide, hermetic carbon, etc.

The lens can be made of transparent or optical filter material and may be coated with optical material.

The excitation light source can be lasers, LEDs, arc lamps, incandescent lamps, mercury lamp, etc.

One or more excitation light sources with same wavelength can be used.

One or more excitation light sources with different wavelengths can be used.

The excitation light can illuminate all or part of the flow through waveguide.

The filters can be longpass, shortpass, colored glass, dichroic filter, or bandpass type of filters or combinations thereof.

There can be one or more filters before the detector.

There can be one or more lenses before the detector.

The flow through waveguide can have portions that are uniform in cross-section and portions where the cross-section changes.

The instrument can include more than one flow through waveguide. It can also include a flow through waveguide for reference.

Since the instrument can also detect the excitation light, absorbance of the excitation light by the sample and/or emission reagent can be detected and reported.

The sample can contain more than one fluorescent material, and the detection can be multiplexed using excitation of appropriate wavelengths and detector(s) with appropriate filters to differentiate the signals associated with the various different emission wavelengths.

The signal for the luminescence and fluorescence can be read repeatedly in time.

The instrument may provide a temperature controlled environment for the flow through waveguide. For example, the temperature can be held at a constant value. For another application, the temperature can be increased up to one value and then changed to another value at a later time. For another application, the temperature can be cycled between two or more temperatures. The temperature and the duration can be programmed by the user.

For absorbance applications, an excitation source is used, but filters may or may not be needed between the flow through waveguide and the detector.

Examplary Implementations

Two exemplary implementations of the flow through Integrating Waveguide Sensor according to certain exemplary embodiments of the present invention and associated experimental data are described below.

Figure 17:
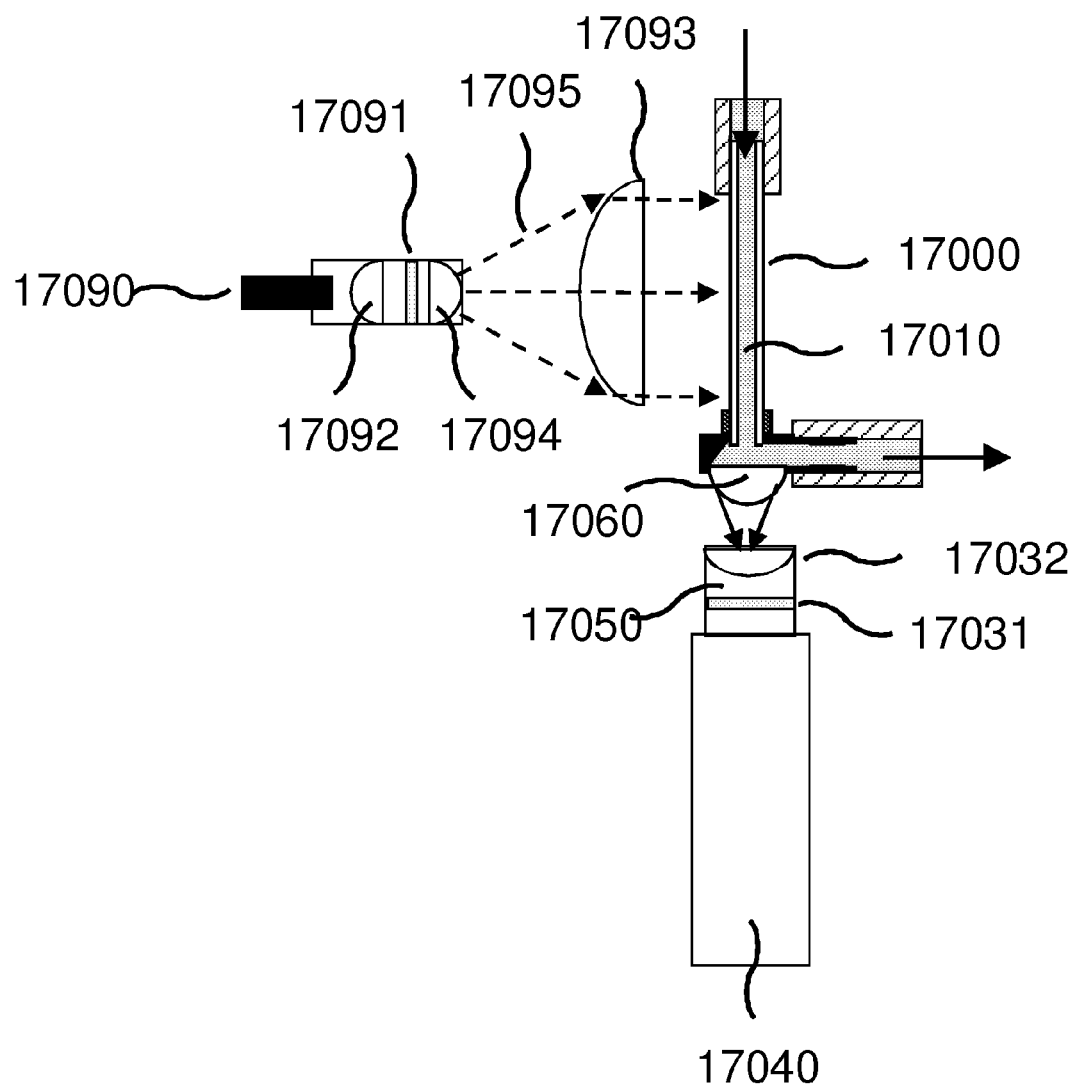
FIG. 17. Schematic of an exemplary implementation of an embodiment of the present invention that can be used as a fluorometer.

In an exemplary implementation of an exemplary embodiment of the present invention, a fluorometer that utilizes a laser 17090 as the excitation light source, as shown in FIG. 17. Referring to FIG. 17, the flow through waveguide is a capillary tube connected to a lens at the end. The excitation light source is a laser. The emission signal is collected at the end of the flow through waveguide. After focusing by lens(es) and passing through filter(s), the light enters the spectrometer detector. The spectrometer gathers the signal of both the excitation and emission wavelengths. A lens 17092 is used to produce parallel light through a laser clean-up filter 17091. The laser light is expanded in one dimension using a lens 17094, and then collimated by another lens 17093 before it impinges on the flow through waveguide 17000. The emitted fluorescent light is collected at the end of the flow through waveguide. It is detected by a spectrometer 17040, after being focused by lenses 17060 and 17032 and passing through a filter 17031. The signal can be collected once or collected repeatedly over a prescribed period. The instrument can be designed to detect a number of samples and a reference in one procedure.

Figure 18:
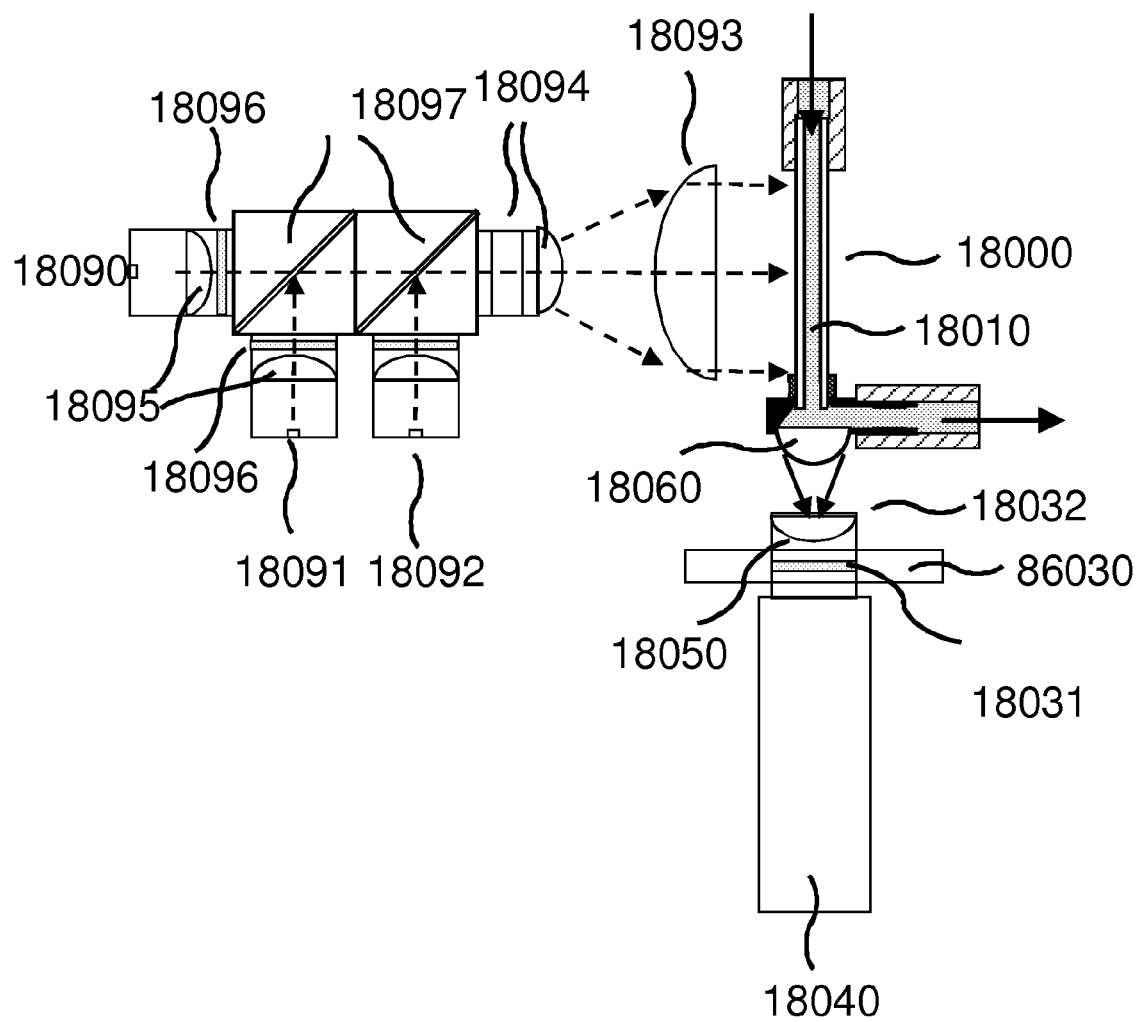
FIG. 18. Schematic of another exemplary implementation of an embodiment of the present invention including an instrument that can be used as a luminometer, fluorometer and photometer.

Another exemplary implementation of certain exemplary embodiment of the present invention includes a combined luminometer and fluorometer instrument that utilizes light emitting diodes (LEDs) as the excitation light source, as shown in FIG. 18. Referring to FIG. 18, The flow through waveguide is a capillary tube connected to a lens at the end. The excitation light source consists of set of three or more LEDs. The signal is collected at the end of the flow through waveguide. After focusing by lens(es) and passing through a filter or set of filters in a filter wheel, the light enters the spectrometer. The spectrometer gathers the signal of both the excitation and emission wavelengths. The light from each LED 18090, 18091 and 18092 is collimated by lenses 18095 into parallel rays. The filter 18096 allows a band of wavelength of the LED light to pass and significantly reduces the transmission of radiation outside the band. This band of wavelength is directed towards the flow through waveguide via a set of dichroic filters 18097 and a set of beam shaping lenses 18093 and 18094 to produce illumination on the flow through waveguide 18000 at nearly a 90 degree angle of incidence to the surface of the flow through waveguide. The LEDs are arranged in the sequence of longer to shorter wavelength corresponding to left to right in FIG. 18. The dichroic filters 18097 allow the reflection of the wavelength of interest and transmit the longer wavelengths in the configuration shown in FIG. 18. After exiting the dichotic filters, the LED light is shaped using lenses to match the shape of the flow through waveguide. A set of three LEDs allows the use of at least three different dyes. The emitted and excitation light are collected at the end of the flow through waveguide. The light is detected by a spectrometer after being focused by a lens and passing through a filter or a set of filters mounted in a filter wheel.

The number of band of wavelength can be one to any desirable number depending on the need.

In an exemplary implementation as shown in FIG. 18, the instrument can be used as a luminometer, where the LEDs will not be illuminated, and the filter wheel, part of the optical elements 18030 can be rotated to a position of no filter when the emission signal data are collected. The signal can be collected once or collected repeatedly over the duration of luminescence.

In an exemplary implementation as shown in FIG. 18, the instrument can be used as a fluorometer, where three fluorescent dyes can be detected within the same flow through waveguide. For example, the LEDs can provide excitation wavelengths, for example, 630 nm, 590 nm, and 470 nm. The filter wheel will include long pass filters corresponding to the LEDs. The spectrometer collects light over a range from, for example, 400 to 750 nm. Four fluorescent dyes that can be excited in sequence by turning on one LED at a time with the appropriate selection of filter in the filter wheel. The appropriate signal is obtained in the wavelength region corresponding to the emission reagent.

In an exemplary implementation as shown in FIG. 18, the instrument can be used as a photometer, where absorbance of excitation light by the sample is obtained by comparing the result of the sample with a reference in the wavelength region of the LED. The appropriate LED can be turned on, but no filter may be needed in the filter wheel to allow the LED light to reach the spectrometer. Data will also be collected from a reference sample to obtain the amount of absorbance.

In an exemplary implementation as shown in FIG. 18, the instrument can be designed to detect a number of samples and a reference in one procedure.

The second embodiment of the instrument can be designed to include alternative LED wavelengths, and/or a greater or lesser number of LEDs.

An exemplary application of certain embodiments of the flow through Integrating Waveguide Sensor according to the present invention is to monitor the concentration of chemicals in a chemical plant. Emission signal can be monitored on a continuous basis.

Another exemplary application of certain embodiments of the flow through Integrating Waveguide Sensor according to the present invention is for detection of target pathogens in a large sample of agricultural produce wash. The inside surface of a flow through capillary can be coated with antibodies to capture the target pathogen in the produce wash. The produce wash is passed through the flow through waveguide, and the target pathogens are captured on the flow through waveguide. Afterwards, the flow through waveguide is washed. There are two methods to produce emission signal. (1) Detector antibody conjugated with luminescent material, such as luciferin, is introduced into the flow through waveguide. After appropriate amount of time for incubation, the flow through waveguide is washed and adenosine triphosphate (ATP) and luciferase are introduced. The three chemicals, luciferin, ATP and luciferase, react to produce luminescence, which can be detected without any filters. (2) A material is introduced into the flow though waveguide to lyse the cells captured on the inside surface of the waveguide. If the cells were alive, they contain ATP. luciferin and luciferase can be introduced subsequently. The three chemicals, luciferin, ATP and luciferase, react to produce luminescence, which can be detected without any filters.

Figure 19A:
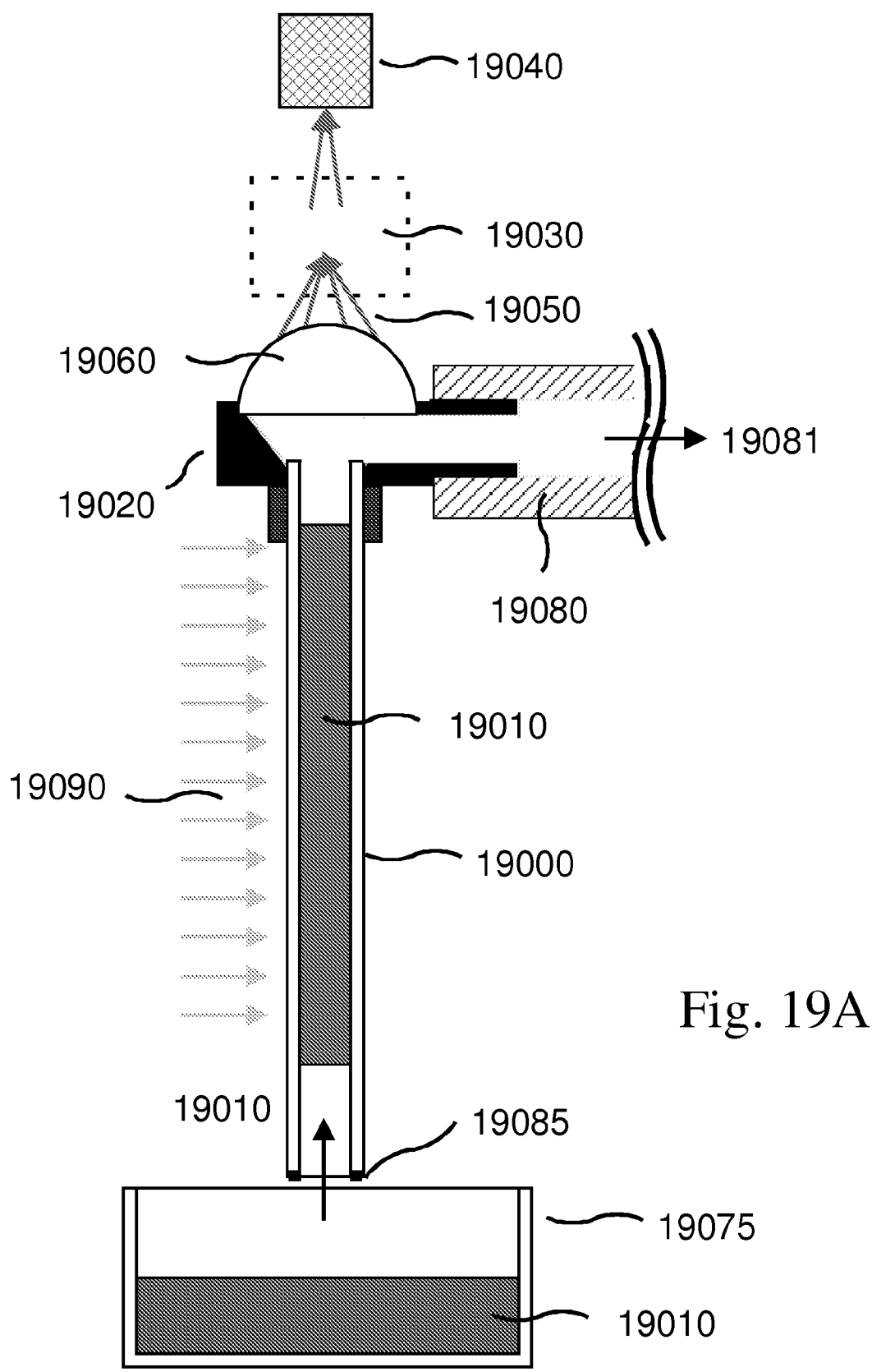
FIG. 19 (a) Schematic side view of fluorescence/absorbance flow through detection system according to an exemplary embodiment of the present invention, where a sample is obtained from a microplate well or other sample containers to fill at least a portion of the waveguide. Excitation light impinges nearly perpendicular to the waveguide. (b) Schematic showing the washing of the waveguide assembly. (c) shows the waveguide empty. (d) a schematic side view of a fluorescence/absorbance flow through detection system according to an exemplary embodiment of the present invention including a plurality (two in this exemplary illustration) of waveguide assemblies.
Figure 19B:
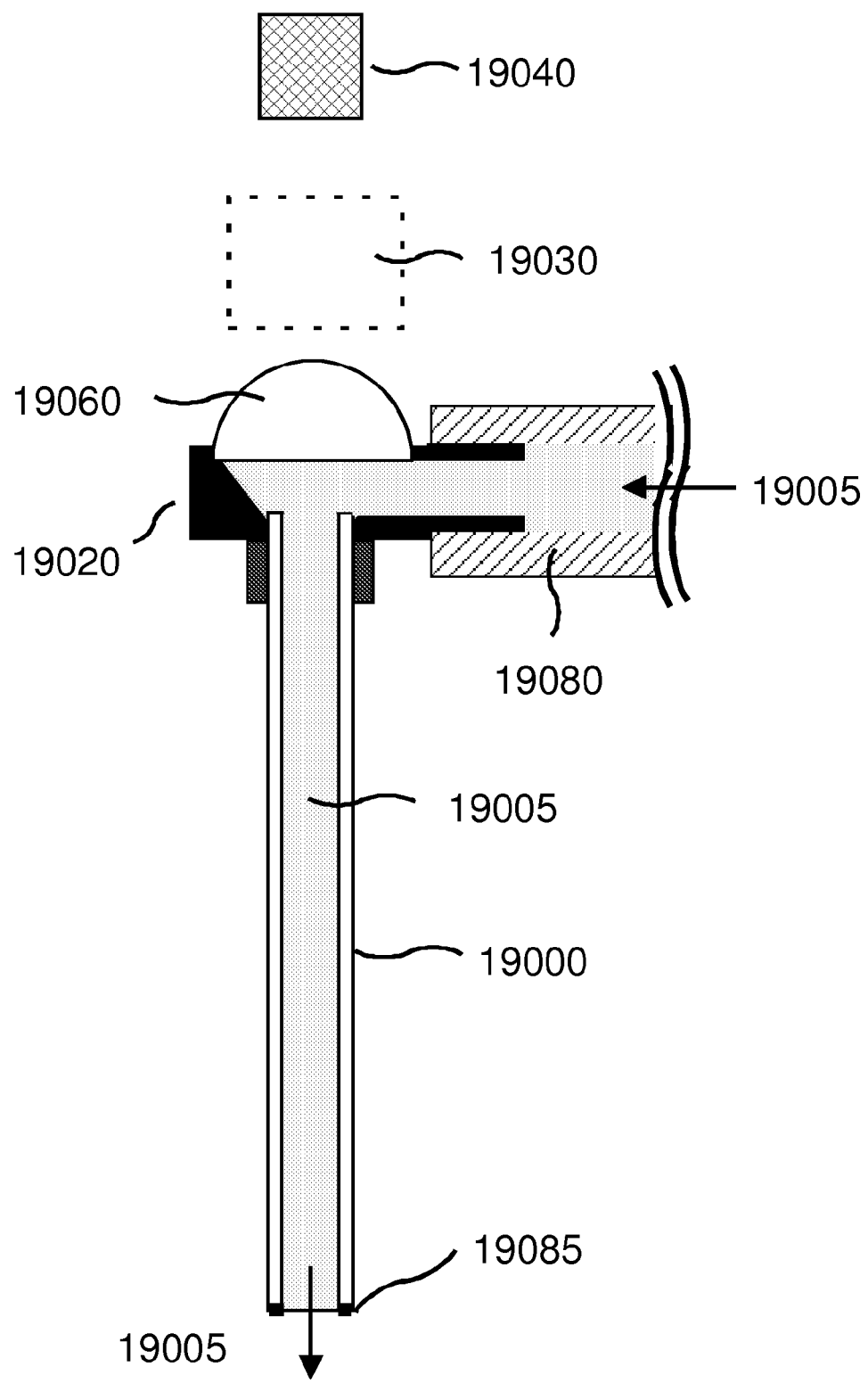

Another exemplary application of the flow through Integrating Waveguide Sensor is to apply to reading arrays of plates, such as 24-well (for example, (3×8) (300 µl) well microplate), 48-well (for example, (6×8) (300 µl) well microplate), 96-well (for example, (8×12) (200 µl) well microplate), 384-well (for example, (16×24) (100 µl) well microplate) and 1536-well (for example, (32×48) (10 µl) well microplate) microplates. FIG. 19A illustrates one implementation of this application. The sample 19010 is in a well or reservoir 19075. The waveguide 19000 is inserted into the well 19075 to suck (in direction 19081) a portion of the sample 19010 by a pump (not shown) connected to the tubing 19080. The waveguide is repositioned to the appropriate height to receive the excitation light 19090 at approximately 90° to the waveguide 19000 and to send the emitted light 19050 through the lens 19060 and any additional optional optical elements (filters and maybe additional lenses) 19030 to the detector 19040. A system including a plurality of waveguide assemblies is illustrated in the example of FIG. 19B, which shows two assemblies each having waveguide 19000, connector 19020, lens 19060, and well 19075 for respective samples 19010 and 19011.

A waveguide assembly that includes a waveguide 19000, the connector 19020 and lens 19060 (as illustrated in the example of FIG. 19), can be designated for each well, but a more efficient and cost effective method is to allow such a waveguide assembly to be reusable. According to an exemplary embodiment of the present invention, to facilitate reuse, the waveguide assembly is configured to be washed by an appropriate wash solution 19005, as shown in FIG. 19B. Examples of wash solutions are deionized water and PBS buffer. According to an exemplary implementation, direction of flow of a wash solution is such that it exits at the open end of the waveguide (as shown by the arrows of FIG. 19B) to a waste container (not shown).

Figure 19C:
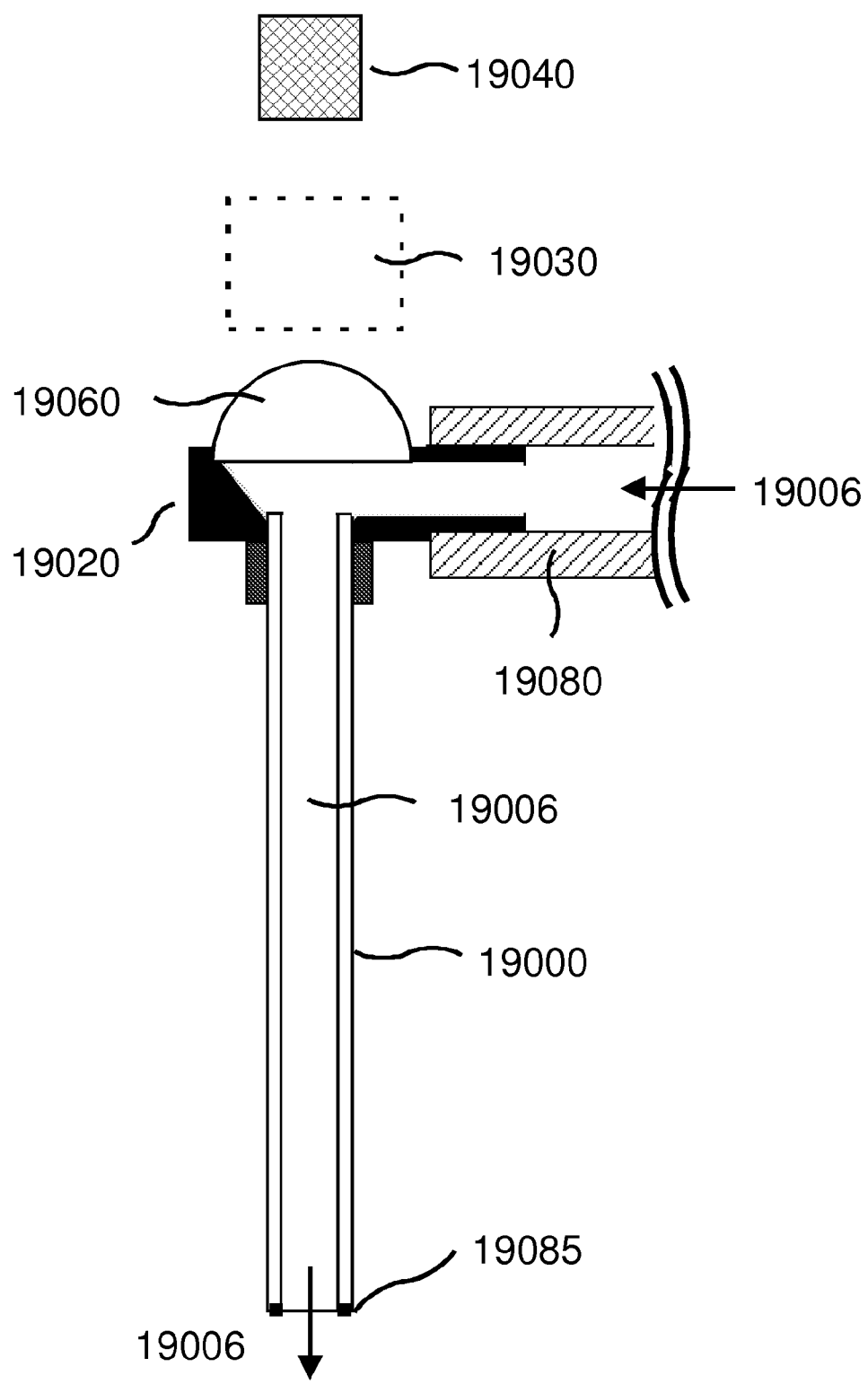
Figure 19D:
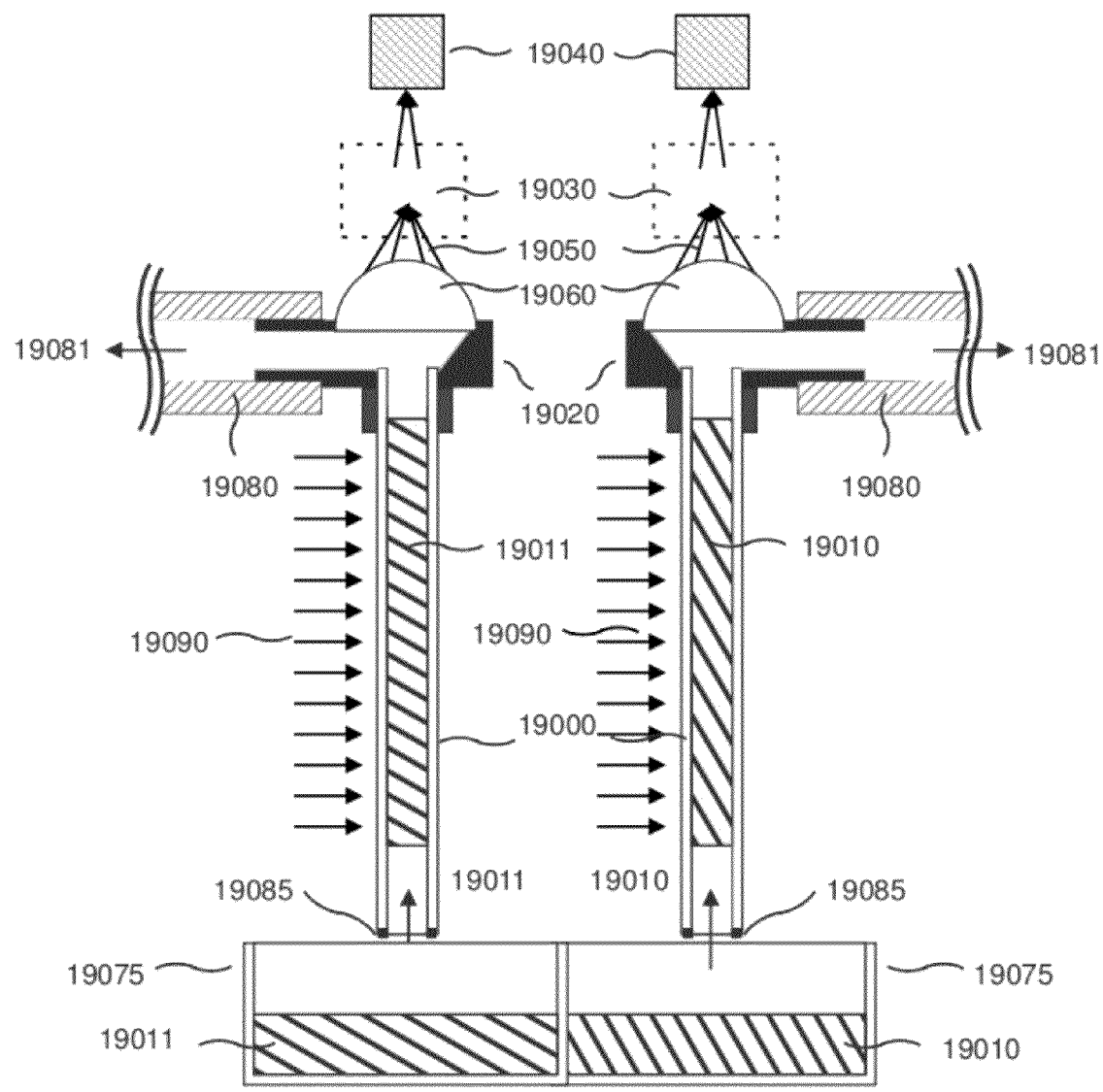

According to exemplary implementation, after washing, all of the wash solution should be removed from the waveguide assembly and the waveguide assembly should be filled with air 19006, as shown in FIG. 19C. Upstream from tubing 19080, valve (not shown) to air is opened, while the valve (not shown) to the wash solution is closed.

Figure 20:
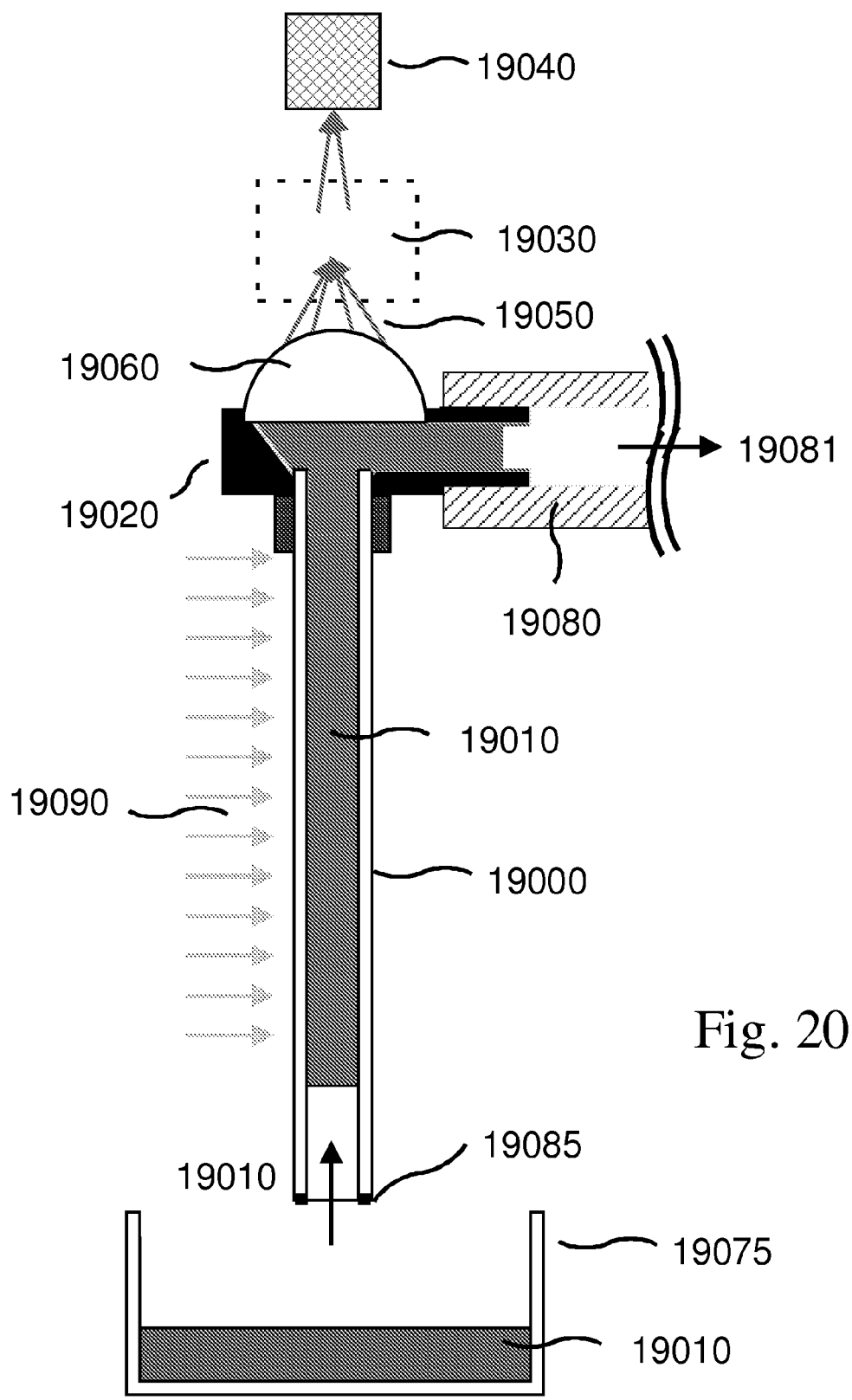
FIG. 20. Schematic side view of fluorescence/absorbance flow through detection system according to an exemplary embodiment of the present invention, where a sample is obtained from a microplate well or other sample containers to fill at least a portion of the waveguide and the connector chamber.

The sample 19010 can be introduced beyond the waveguide 19000 into the region of connector 19020, as shown in FIG. 20.

Figure 21:
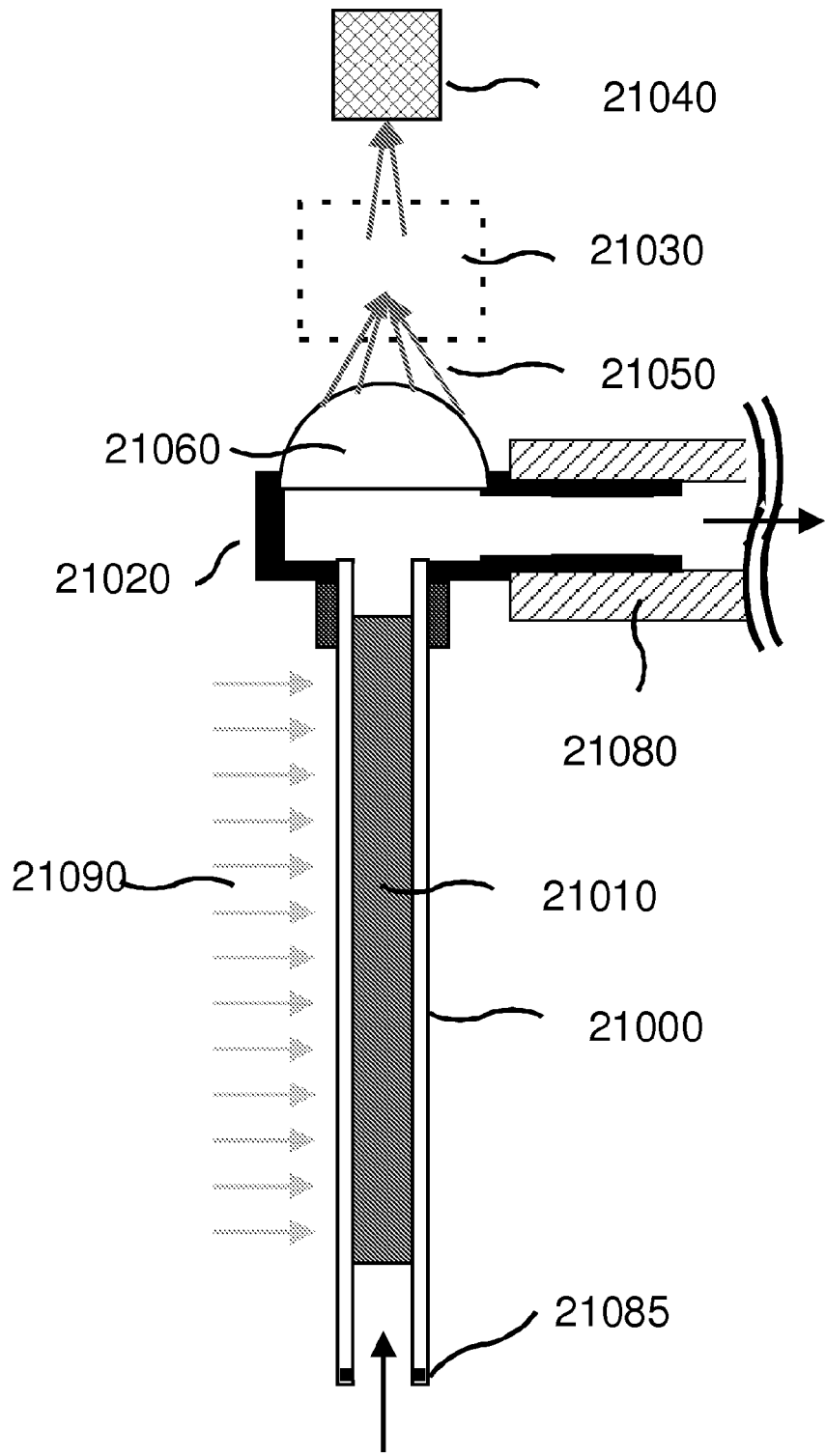
FIG. 21. Schematic side view of fluorescence/absorbance flow through detection system according to another exemplary embodiment of the present invention, where a sample is obtained from a microplate well or other sample containers to fill at least a portion of the waveguide utilizing an alternative connector to the waveguide.
Figure 22:
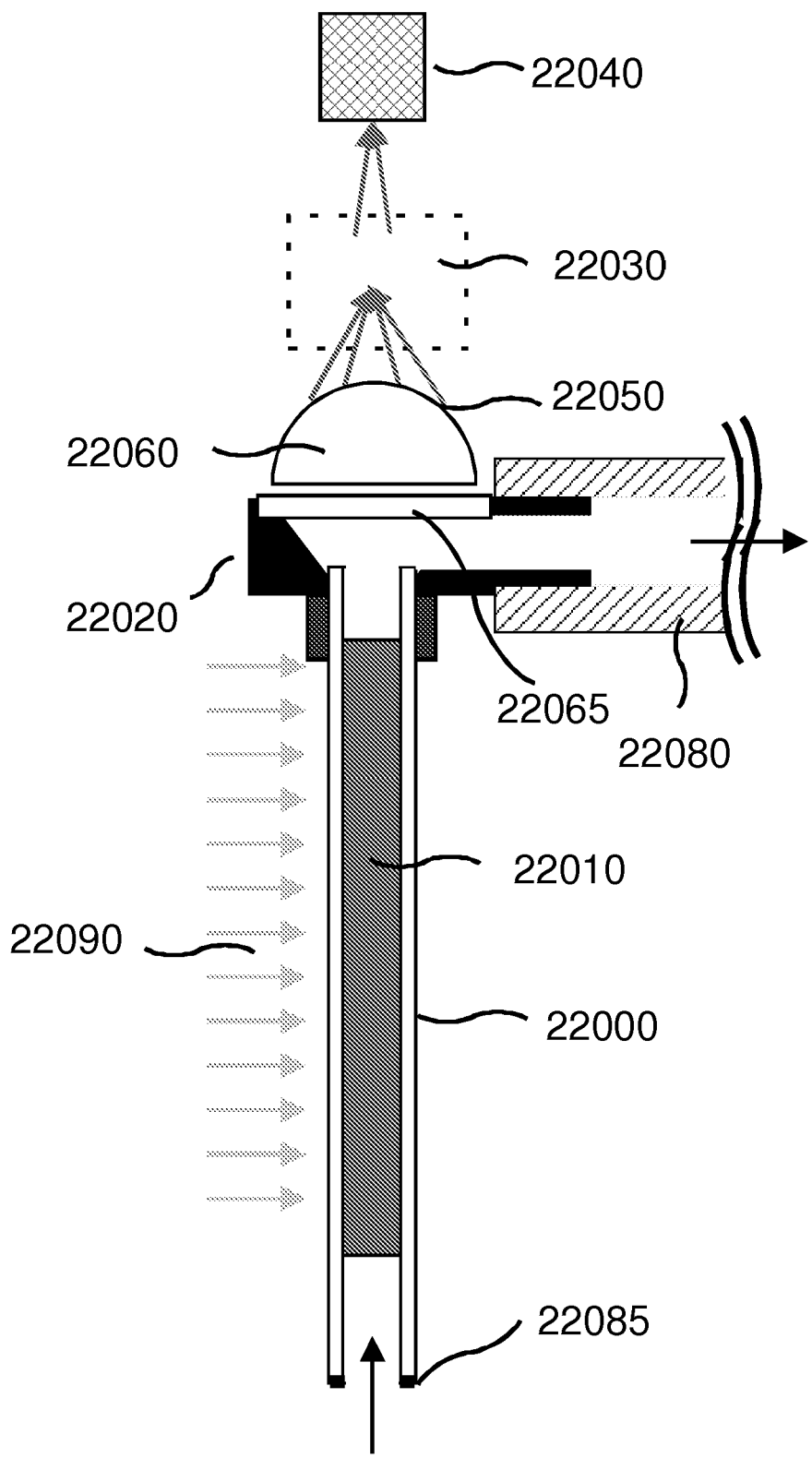
FIG. 22. Schematic side view of fluorescence/absorbance flow through detection system according to another exemplary embodiment of the present invention, where a sample is obtained from a microplate well or other sample containers to fill at least a portion of the waveguide, where the lens is not part of the connector.
Figure 23:
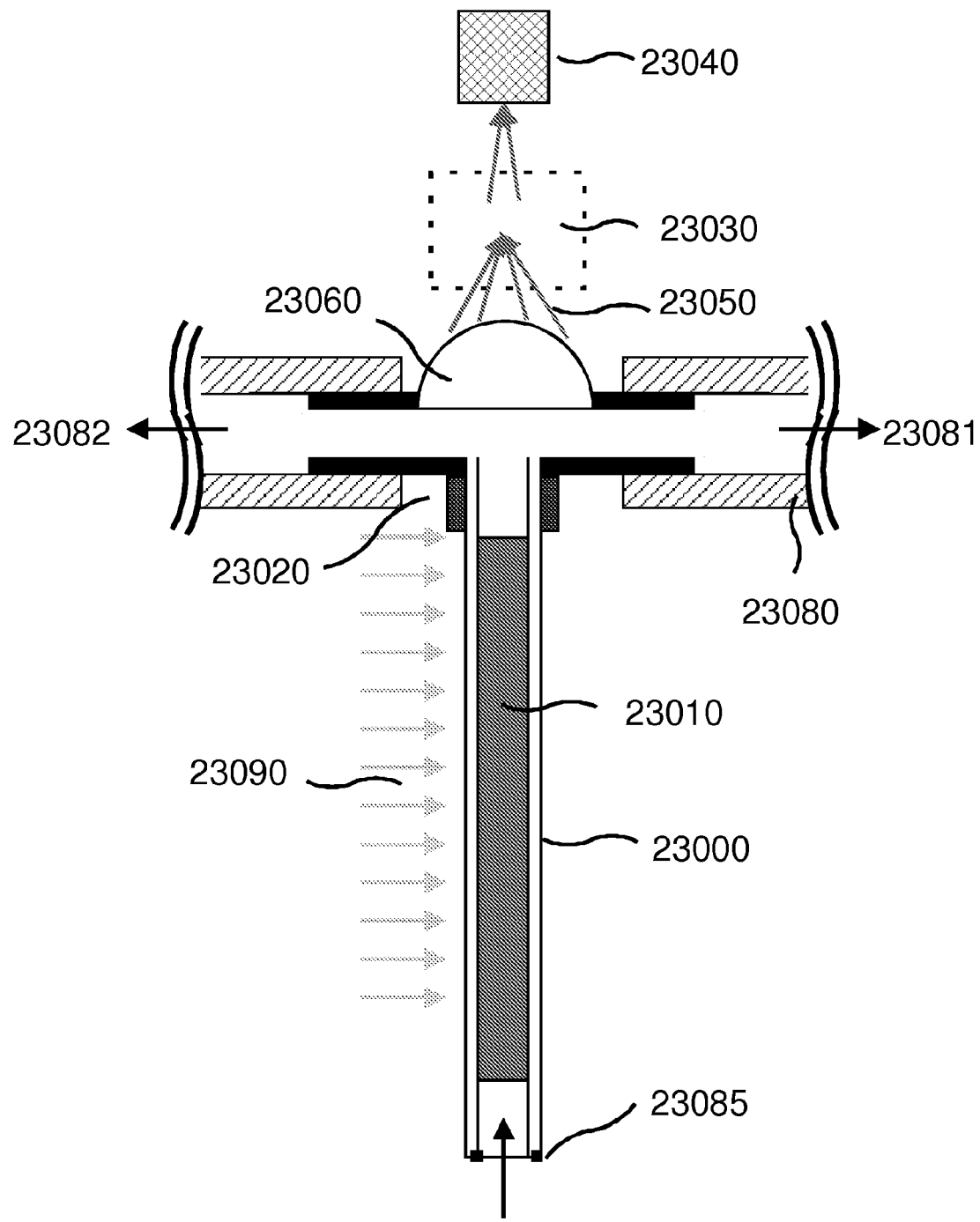
FIG. 23. Schematic side view of fluorescence/absorbance flow through detection system according to another exemplary embodiment of the present invention, where a sample is obtained from a microplate well or other sample containers to fill at least a portion of the waveguide, where connector is attached to the wash reservoir at one end and open to air at another end.
Figure 24:
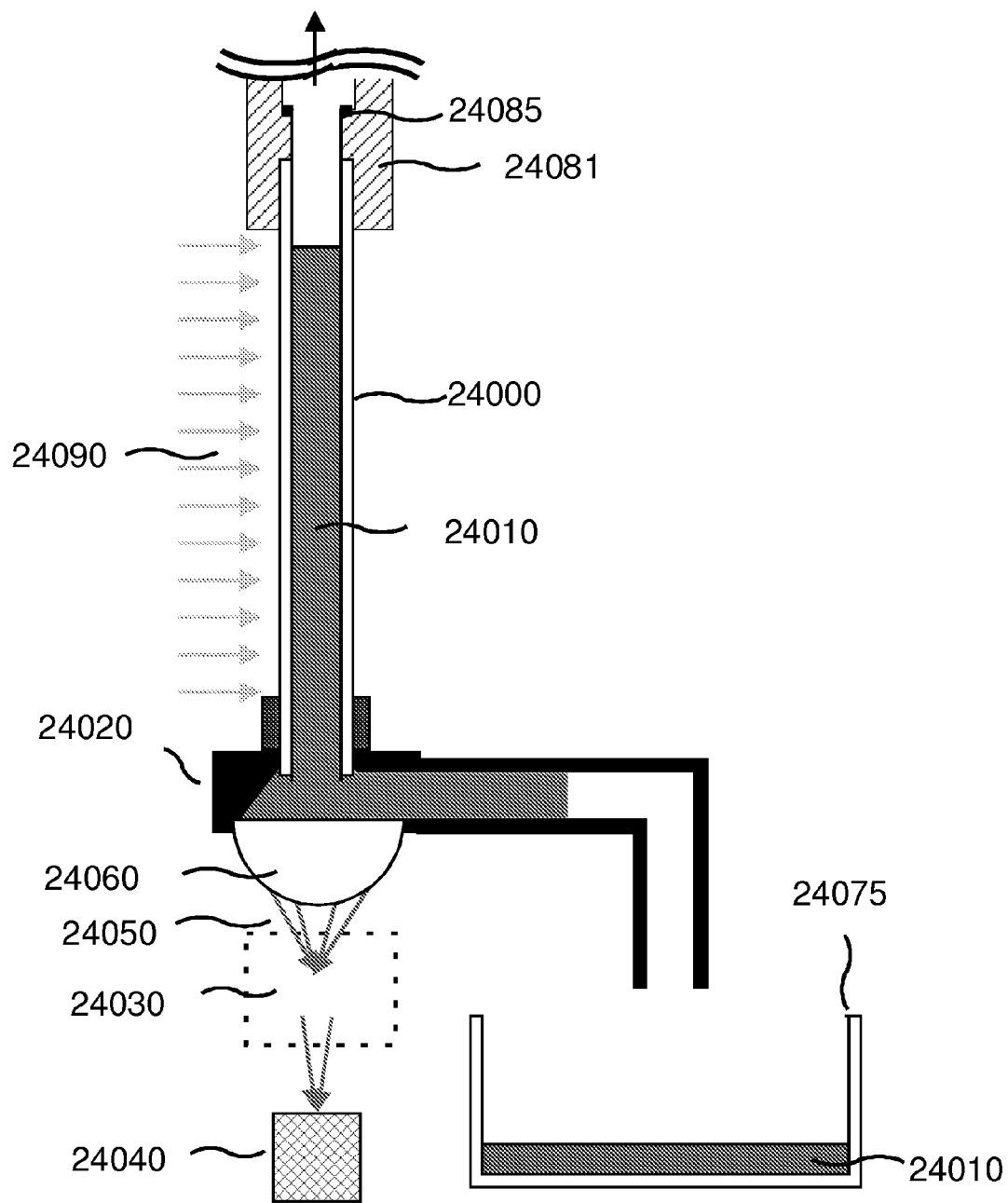
FIG. 24. Schematic side view of fluorescence/absorbance flow through detection system according to another exemplary embodiment of the present invention, where a sample is obtained from a microplate well or other sample containers to fill at least a portion of the waveguide, where the sample is obtained from the well through the connector.

There can be many ways to implement the waveguide assembly. In FIG. 21, an exemplary difference is the shape of the connector 21020. In FIG. 22, the waveguide assembly 22020 uses a piece of clear flat material 22065, such that the lens 22060 is not required to be attached to the assembly 22020. In FIG. 23, the waveguide assembly 23020 has two ports, port 23081 for wash solution and port 23082 for air. In. FIG. 24, the sample 24010 is pumped into the waveguide 24000 through an exemplary connector 24020 from reservoir 24075.

Figure 25:
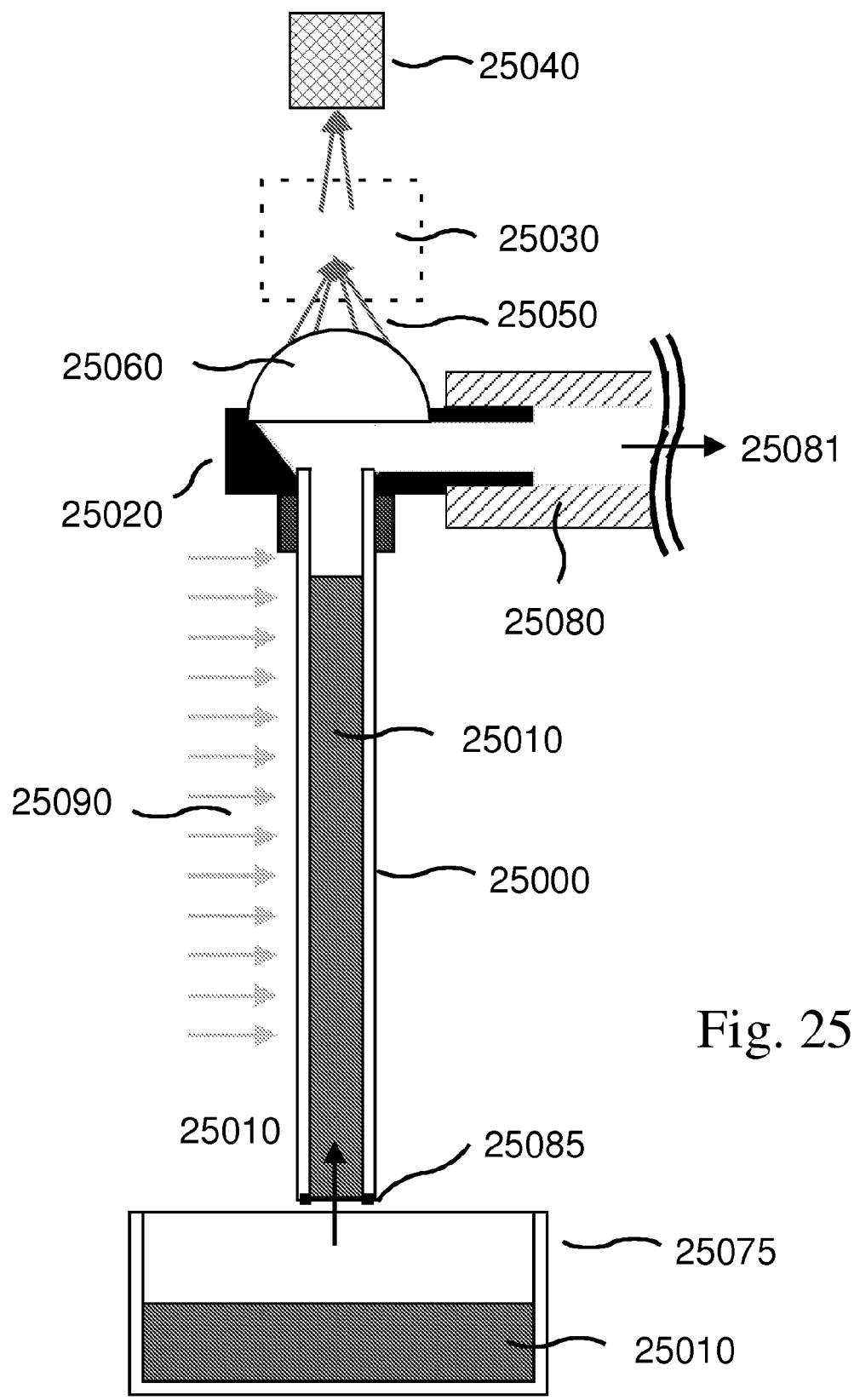
FIG. 25. Schematic side view of fluorescence/absorbance flow through detection system according to another exemplary embodiment of the present invention, where a sample is obtained from a microplate well or other sample containers to fill at least a portion of the waveguide, where the sample is urged into the waveguide by a capillary force.

Instead of the sample pumped into the waveguide, an exemplary implementation of FIG. 25 shows that the liquid sample 25010 can be sucked up by the capillary action with an appropriate diameter of waveguide 25000.

The waveguide assembly can be grouped in format of 8, 12, 16, 24, or more waveguides, and the waveguides are spaced according to the spacing of the microplate wells. When properly spaced, the format of 8 will be applicable for 24-well (3×8), 48-well (6×8), 96-well (8×12), 384-well (16×24) and 1536-well (36×48) plates. Pumping the sample into the waveguide, introducing the wash solution and removing the wash solution can be performed simultaneously for all the waveguide assemblies.

There can be an array of detectors and excitation sources. For cost purposes, it may be advantageous to have one detector and one excitation light source. Thus, the data for each well is to be collected sequentially.

Figure 26:
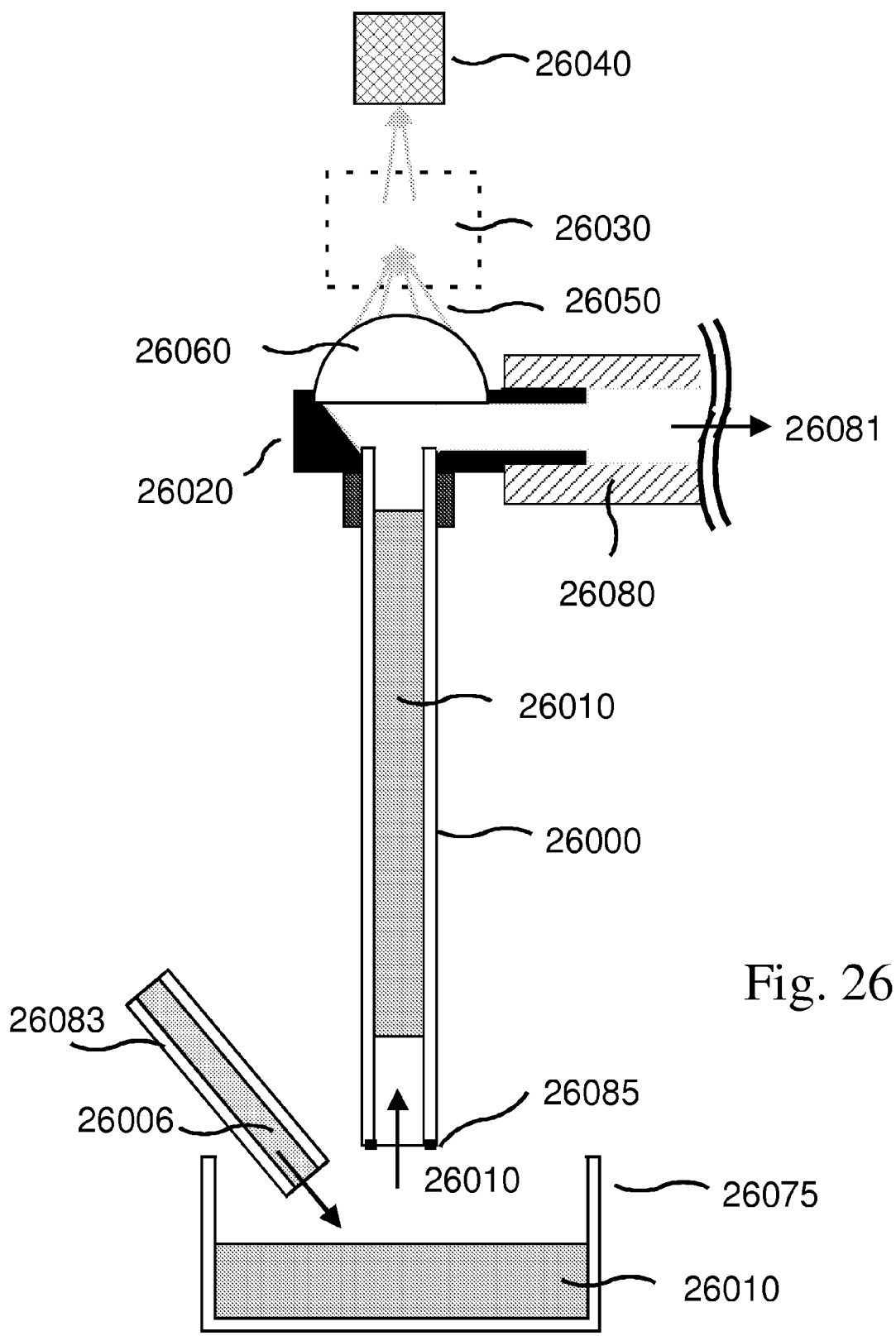
FIG. 26. Schematic side view of luminescence flow through detection system according to another exemplary embodiment of the present invention, where a sample is obtained from a microplate well or other sample containers to fill at least a portion of the waveguide, further including an injector to provide luminescence reagent to the well.

For luminescence application shown in an exemplary implementation of FIG. 26, chemical or biochemical materials 26006 must be added to the well by an injector 26083 to produce emission light by chemical or biochemical reaction. The mixed solution 26010 in the well 26075 is then pumped into the waveguide 26000 to generate the emission signal 26050. There is no need for excitation source in an exemplary luminescence application. There can be one injector for the whole array, or an equal number of injectors as the number of waveguides.

The method of retrieving and testing sample from reservoir using exemplary embodiments in the present invention is not limited to the standard microplate format.

While the invention has been shown and described with reference to certain exemplary embodiments thereof, it will be understood by those skilled in the art that various changes in form and details may be made therein without departing from the spirit and scope of the invention as defined by the appended claims and their equivalents.

We claim:

1. A system comprising:
    a plurality of waveguide assemblies, each of said waveguide assemblies comprising:
        a chamber for accommodating a sample and passing the sample therethrough;
        a distal end providing at least a first access to the chamber; and
        a proximal end comprising at least a light transmissive portion; and
        at least one wall extending from the proximal end to the distal end in a longitudinal direction; and
        wherein the at least one wall is configured to interact with the sample whereby the wall and the sample comprise a waveguide configuration for directing light emitted by the sample toward the proximal end; and
    a reservoir for accommodating the sample therein;
    wherein the sample is delivered from the reservoir into the chamber of the at least one of the waveguide assemblies via the distal end of the least one of the waveguide assemblies,
    the proximal end comprises a connector, said connector comprising the light transmissive portion, and
    the light transmissive portion comprises a lens for focusing the light emitted by the sample directed by the waveguide configuration toward the proximal end.

2. The system of claim 1, further comprising a light source configured to emit light for illuminating the chamber of at least one of the waveguide assemblies at an angle of approximately 90 degrees with respect to the outer longitudinal surface of the chamber.

3. The system of claim 2, wherein the light source comprises at least one of a single light source, a series of light emitting diodes (LEDs) and a laser.

4. The system of claim 3 wherein the single light source generates near UV and visible lights, the system further comprising band pass filters configured to select specific wavelength of light output from the light source.

5. The system of claim 3, wherein the LEDs comprise high power LEDs, the system further comprising band pass filters configured to select specific wavelength of light output from the LEDs.

6. The system of claim 1, wherein at least one of the distal end and the proximal end of at least one of the waveguide assemblies is configured to receive a wash solution.

7. The system of claim 6, wherein the wash solution passes through the chamber of the at least one of the waveguide assemblies.

8. The system of claim 7, wherein a flow direction of the wash solution through the chamber of the at least one of the waveguide assemblies is opposite to a flow direction of the sample.

9. The system of claim 6, wherein the at least one of the waveguide assemblies is configured for repeated introduction of the sample and repeated receiving of the washing solution, whereby the at least one of the waveguide assemblies is configured for repeated use.

10. The system of claim 1, further comprising an emission detector configured with respect to at least one of the waveguide assemblies to detect light output from the light transmissive portion of the proximal end of the at least one of the waveguide assemblies.

11. The system of claim 10, wherein the emission detector comprises at least one of a spectrometer, a PMT or photo diode, and a CCD.

12. The system of claim 1, comprising a configuration of one of 8, 12, 16, or 24 of said waveguide assemblies configured to retrieve sample from 8, 12, 16 or 24 reservoirs at a time, respectively.

13. The system of claim 1, further comprising a plurality of reservoirs, wherein at least one of said waveguide assemblies is configured to retrieve samples from said plurality of reservoirs one sample at a time.

14. The system of claim 1, wherein the reservoir comprises one of a 24-well, a 48-well, a 96-well, a 384 well, or a 1536-well microplate configurations.

15. The system of claim 14, wherein the 24-well microplate comprises a 3×8 microplate configuration, a 48-well microplate comprises a 6×8 microplate configuration, a 96-well microplate comprises a 8×12 microplate configuration, a 384 well microplate comprises a 16×24 microplate configuration, and a 1536-well microplate comprises a 32×48 microplate configuration.

16. The system of claim 1, further comprising a lens configured with respect to the light transmissive portion for focusing the light transmitted through the light transmissive portion.

17. The system of claim 1, wherein the connector comprises transmissive material integrally forming the light transmissive portion.

18. The system of claim 1, wherein the connector comprises transmissive material integrally forming the light transmissive portion comprising said lens.

19. The system of claim 1, wherein the waveguide assemblies are configured for packaging as a group.

20. The system of claim 1, wherein the waveguide assemblies are configured for packaging as a group, and at least one of the waveguide assemblies packaged as the group comprises said lens.

21. The system of claim 1, wherein the at least one wall comprises a reflective coating at least in the vicinity of said distal end.

22. The system of claim 1, further comprising a pump connected to at least one of the waveguide assemblies,
    wherein the pump facilitates the delivery of the sample from the reservoir into the chamber of the at least one of the waveguide assemblies.

23. The system of claim 1, wherein a capillary action of the chamber facilitates delivery of the sample from the reservoir into the chamber of the at least one of the waveguide assemblies.

24. A flow through waveguide assembly comprising:
    a chamber for accommodating a sample and passing the sample therethrough;
    a distal end providing at least a first access to the chamber; and
    a proximal end comprising at least a light transmissive portion;

at least one wall extending from the proximal end to the distal end in a longitudinal direction; and a connector comprising the light transmissive portion;

wherein the at least one wall is configured to interact with the sample whereby the wall and the sample comprise a waveguide configuration for directing light emitted by the sample toward the proximal end, and the light transmissive portion comprises a lens focusing the light emitted by the sample directed by the waveguide configuration toward the proximal end.

25. The flow through waveguide assembly of claim 24, further comprising a lens configured with respect to the light transmissive portion for focusing the light transmitted through the light transmissive portion.

26. The flow through waveguide assembly of claim 24, wherein the connector comprises transmissive material integrally forming the light transmissive portion.

27. The flow through waveguide assembly of claim 24, wherein the connector comprises transmissive material integrally forming the light transmissive portion comprising said lens.

28. The flow through waveguide assembly of claim 24, wherein the at least one wall comprises a reflective coating at least in the vicinity of said distal end.

29. The flow through waveguide assembly of claim 24, wherein the at least one wall comprises a reflective coating on external surface thereof.

30. The flow through waveguide assembly of claim 24, wherein the sample comprises one of liquid or gas.

* * * * *